(12) United States Patent
Knudson et al.

(10) Patent No.: US 6,361,519 B1
(45) Date of Patent: Mar. 26, 2002

(54) MESH TIP MYOCARDIAL IMPLANT

(75) Inventors: Mark B. Knudson, Shoreview, MN (US); William L. Giese, Arlington, VA (US)

(73) Assignee: HeartStent Corporation, St. Paul, MN (US)

( * ) Notice: Subject to any disclaimer, the term of this patent is extended or adjusted under 35 U.S.C. 154(b) by 0 days.

(21) Appl. No.: 09/548,175

(22) Filed: Apr. 13, 2000

Related U.S. Application Data

(63) Continuation of application No. 09/055,488, filed on Apr. 3, 1998, now Pat. No. 6,093,166, which is a continuation of application No. 08/689,773, filed on Aug. 13, 1996, now Pat. No. 5,755,682.

(51) Int. Cl.[7] .................. A61M 5/00; A61M 39/00; A61F 2/04; A61F 2/06
(52) U.S. Cl. ................. 604/8; 606/151; 623/1.1; 623/1.12; 600/16
(58) Field of Search .................. 604/8; 606/151; 623/1.1, 1.12; 600/16

(56) References Cited

U.S. PATENT DOCUMENTS

| | | |
|---|---|---|
| 2,127,903 A | 8/1938 | Bowen |
| 3,042,021 A | 7/1962 | Read |
| 3,995,617 A | 12/1976 | Watkins et al. |
| 4,086,665 A | 5/1978 | Poirier |
| 4,118,806 A | 10/1978 | Poirier |
| 4,546,499 A | 10/1985 | Possis et al. |
| 4,562,597 A | 1/1986 | Possis et al. |
| 4,581,017 A | 4/1986 | Sahota |
| 4,712,551 A | 12/1987 | Rayhanabad |
| 4,769,031 A | 9/1988 | McGough et al. |

(List continued on next page.)

FOREIGN PATENT DOCUMENTS

| | | |
|---|---|---|
| EP | 0 515 867 A2 | 12/1992 |
| RU | 2026640 C1 | 1/1995 |
| SU | 1754128 A1 | 8/1992 |
| WO | WO 93/00868 | 1/1993 |
| WO | WO 95/35065 | 12/1995 |

(List continued on next page.)

OTHER PUBLICATIONS

Tea E. Acuff, M.D. et al., *Minimally Invasive Coronary Artery Bypass Grafting*, 61 Annals Of Thoracic Surgery 135–137 (1996).

Andrews et al., *Assessment of Feasibility for Endovascular Prosthetic Tube Correction of Aortic Aneurysm*, 82 Brit. J. of Surgery 917–919 (1995).

Kit V. Arom, M.D, Ph.D. et al., *Patient Characteristics, Safety, and Benefits of Same–Day Admission for Coronary Artery Bypass Grafting*, 61 Annals Of Thoracic Surgery 1136–1140 (1996).

Toshiyuki Beppu, ME et al., *A Computerized Control System for Cardiopulmonary Bypass*, 109 J. Thoracic & Cardiovascular Surery 428–438 (Mar. 1995).

Black, Martin M. et al., *Design and Flow Characteristics*, p. 4, Replacement Cardiac Valves, Bodner, Endre et al., Editors, Pergamon Press (1991) (title page, p. v and p. 4 reproduced).

(List continued on next page.)

*Primary Examiner*—Corrine McDermott
*Assistant Examiner*—Choon P. Koh
(74) *Attorney, Agent, or Firm*—Merchant & Gould P.C.

(57) ABSTRACT

A method and apparatus for performing coronary artery bypass surgery establishes a channel leading directly from a chamber of a heart into a coronary artery. The coronary artery bypass procedure may be performed with or without cardiopulmonary bypass.

28 Claims, 14 Drawing Sheets

U.S. PATENT DOCUMENTS

| | | | |
|---|---|---|---|
| 4,788,975 | A | 12/1988 | Shturman et al. |
| 4,861,330 | A | 8/1989 | Voss |
| 4,862,886 | A | 9/1989 | Clarke et al. |
| 4,902,289 | A | 2/1990 | Yannas |
| 4,953,553 | A | 9/1990 | Tremulis |
| 4,955,856 | A | 9/1990 | Phillips |
| 4,985,014 | A | 1/1991 | Orejola |
| 4,995,857 | A | 2/1991 | Arnold |
| 5,054,484 | A | 10/1991 | Hebeler, Jr. |
| 5,071,406 | A | 12/1991 | Jang |
| 5,143,093 | A | 9/1992 | Sahota |
| 5,190,058 | A | 3/1993 | Jones et al. |
| 5,209,731 | A | 5/1993 | Sterman et al. |
| 5,254,097 | A | 10/1993 | Schock et al. |
| 5,256,150 | A | 10/1993 | Quiachon et al. |
| 5,275,622 | A | 1/1994 | Lazarus et al. |
| 5,287,861 | A | 2/1994 | Wilk |
| 5,353,744 | A | 10/1994 | Khouri |
| 5,370,685 | A | 12/1994 | Stevens |
| 5,383,925 | A | 1/1995 | Schmitt |
| 5,395,349 | A | 3/1995 | Quiachon et al. |
| 5,409,019 | A | 4/1995 | Wilk |
| 5,425,705 | A | 6/1995 | Evard et al. |
| 5,429,144 | A | 7/1995 | Wilk |
| 5,443,497 | A | 8/1995 | Venbrux |
| 5,452,733 | A | 9/1995 | Sterman et al. |
| 5,458,574 | A | 10/1995 | Machold et al. |
| 5,484,418 | A | 1/1996 | Quiachon et al. |
| 5,489,295 | A | 2/1996 | Piplani et al. |
| 5,501,698 | A | 3/1996 | Roth et al. |
| 5,505,725 | A | 4/1996 | Samson et al. |
| 5,655,548 | A | 8/1997 | Nelson et al. |
| 5,662,124 | A | 9/1997 | Wilk |
| 5,676,696 | A | 10/1997 | Marcade |
| 5,755,682 | A | 5/1998 | Knudson et al. |
| 5,830,222 | A | 11/1998 | Makower |
| 6,005,164 | A | 12/1999 | Makower |
| 6,010,614 | A | 1/2000 | Makower |

FOREIGN PATENT DOCUMENTS

| | | |
|---|---|---|
| WO | WO 96/00033 | 1/1996 |
| WO | WO 96/04854 | 2/1996 |
| WO | WO 96/05773 | 2/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 98/08456 | 3/1998 |

OTHER PUBLICATIONS

Gerald D. Buckberg, MD, *Update on Current Techniques of Myocardial Protection*, 60 Annals Of Thoracic Surery 805–814 (1995).

Enio Buffolo, M.D. et al., *Coronary Artery Bypass Grafting Without Cardiopulmonary Bypass*, 61 Annals Of Thoracic Surgery 63–66 (1996).

Bojan Cercek, M.D. et al., *Growth Factors in Pathogenesis of Coronary Arterial Restenosis*, 68 Am. J. Cardiology 24C–33C (Nov. 4, 1991).

Mark W. Connolly & Robert A. Guyton, *Cardiopulmonary Bypass and Intraoperative Protection*, in Hurst's The Heart 2443–450 (Robert C. Schlant & R. Wayne Alexander eds., 8th ed. 1994).

Michael D. Dake, M.D. et al., *Transluminal Placement of Endovascular Stent—Grafts for the Treatment of Descending Thoracic Aortic Aneurysms*, 331 N.E.J.M. 1729–1734 (Dec. 29, 1994).

Frank M. Galioto, Jr., M.D., et al., *Right Coronary Artery to Left Ventricle Fistula*, 82 American Heart Journal 93–97 (Jul. 1971).

Alfred Goldman, M.D., et al., *Experimental Methods for Producing a Collateral Circulation to the Heart Directly from the Left Ventricle*, 31 J. Thoracic Surg. 364–374 (Mar. 1956).

Hausdorf et al., *Radiofrequency–Assisted "Reconstruction" of the Right Ventricular Outflow Tract in Muscular Pulmonary Atresia with Ventricular Septal Defect*, 69 Br Heart J. 343–346 (1993).

Minoru Hongo, M.D. et al., *Effects of Heart Rate on Phasic Coronary Blood Flow Pattern and Flow Reserve in Patients with Normal Coronary Arteries: A Study with an intravascular Doppler Catheter and Spectral Analysis*, 127 Am. Heart J. 545–551 (Mar. 1994).

Noritake Houki et al., *A Simulation Study of Coronary Circulatory System—A Theoretical Analysis of Intramyocardial Flow Distribution Mechanism*, 41 Japanese Circulation J. (Nov. 1977).

Stuart W. Jamieson, *Aortocoronary Saphenous Vein Bypass Grafting*, in Rob & Smith's Operative Surgery: Cardiac Surgery 454–470 (Stuart W. Jamieson & Norman E. Shumway, eds. , 4th ed. 1986).

Larry R. Kaiser et al., *Video–Assisted Thoracic Surgery: The Current State of the Art*, 165 Am. J. Roentgenology 1111–1117 (Nov. 1995).

Fumihiko Kajiya, M.D., Ph.D. et al., *Mechanical Control of Coronary Artery Inflow and Vein Outflow*, 53 Japanese Circulation J. 431–439 (May 1989).

Fumihiko Kajiya et al., *Endocardial Coronary Microcirculation of the Beating Heart*, in Interactive Phenomena In The Cardiac System, 173–180 (S. Sideman and R. Beyar eds. 1993).

Fumihiko Kajiya et al., *Velocity Profiles and Phasic Flow Patterns in the Non–Stenotic Human Left Anterior Descending Coronary Artery During Cardiac Surgery*, 27 Cardiovascular Res. 845–850 (1993).

Kohmoto, et al., *Does Blood Flow Through Holmium: YAG Transmyocardial Laser Channels?*, 61 Ann. Thorac. Surg. 861–868 (1996).

Louagie et al., *Operative Risk Assessment in Coronary Artery Bypass Surgery, 1990–1993: Evaluation of Perioperative Variables*, 43 Thoracic Cardiovascular Surgeon 134–141 (1995).

Michael L. Marin, M.D. et al., *Initial Experience with Transluminally Placed Endovascular Grafts for the Treatment of Complex Vascular Lesions*, 222 Annals Of Surgery 449–469 (Oct. 1995).

Massimo, M.D., et al., *Myocardial Revascularization by a New Method of Carrying Blood Directly From the Left Ventricular Cavity into the Coronary Circulation*, 34 J. Thoracic Surg. 257–264 (Aug. 1957).

Carmelo A. Milano, M.D. et al., *Mediastinitis After Coronary Artery Bypass Graft Surgery*, 92 Circulation 2245–2251 (Oct. 15, 1995).

Mahmood Mirhoseini, M.D., et al., *New Concepts in Revascularization of the Myocardium*, 45 Annuals of Thoracic Surgery 415–420 (Apr. 1988).

Mirhoseini, M.D., et al., *Myocardial Revascularization by Laser: A Clinical Report*, 3 Lasers in Surgery and Medicine 241–245 (1983).

Ian Munro, et al., *The Possibility of Myocardial Revascularization by Creation of a Left Ventriculocoronary Artery Fistula*, 58 J. Thoracic & Cardiovascular Surgery 25–32 (Jul. 1969).

Nishida, *Flow Study of Surgical Coronary Artery Fistula as an Alternative to Sequential Bypass*, 3 Cardiovascular Surgery 375–380 (Aug. 1995).

Nollert et al., *Use of the Internal Mammary Artery as a Graft in Emergency Coronary Artery Bypass Grafting after Failed PTCA*, 43 Thoracic Cardiovascular Surgeon 142–147 (1995).

Roque Pifarre, M.D., et al. *Myocardial Revascularization from the Left Ventricle: A Physiologic Impossibility*, 19 Surgical Forum 157–159 (1968).

Prospectus of CardioGenesis Corporation, May 21, 1996, pp. 1–59.

Prospectus of Cardio Thoracic Systems, Apr. 18, 1996, pp. 1–61, F1–F20.

Prospectus of Cardio Thoracic Systems, Inc., May 22, 1996, pp. 1–7.

Prospectus of Heartport, Apr. 25, 1996, pp. 1–64, F1–F15.

Martin Schneider, M.D. et al., *Transcatheter Radiofrequency Perforation and Stent Implantation for Palliation of Pulmonary Atresia in a 3060-g Infant*, 34 Catheterization And Cardiovascular Diagnosis 42–45 (1995).

Daniel S. Schwartz, M.D. et al., *Minimally Invasive Cardiopulmonary Bypass with Cardioplegic Arrest: A Closed Chest Technique with Equivalent Myocardial Protection*, 111 J. Thoracic & Cardiovascular Surgery 556–566 (Mar. 1996).

Jerome Segal, M.D. et al., *Alterations of Phasic Coronary Artery Flow Velocity in Humans During Percutaneous Coronary Angioplasty* 20 J. Am. College Of Cardiology 276–286 (Aug. 1992).

Ludwig K. Von Segesser, Arterial Grafting For Myocardial Revascularization: Indications, Surgical Techniques And Results 4–5, 38–39, 48–80 (1990).

Ulrich Sigwart, *An Overview of Intravascular Stents: Old and New*, in 2 Topol's Textbook Of Interventional Cardiology 803–815 (Eric J. Topol ed., 2nd ed. 1994).

George Silvay, M.D., Ph.D. et al., *Cardiopulmonary Bypass for Adult Patients: A Survey of Equipment and Techniques*, 9 J. Of Cardiothoracic & Vasuclar Anesthesia 420–424 (Aug. 1995).

John H. Stevens, M.D. et al., *Port–Access Coronary Artery Bypass Grafting: A Proposed Surgical Method*, 111 J. Thoracic & Cardiovascular Surgery (Mar. 1996).

Mark Vierra, M.D., *Minimally Invasive Surgery*, 46 Ann. Rev. Med. 147–158 (1995).

Vineberg, M.D., et al., *Treatment of Acute Myocardial Infarction by Endocardial Resection*, 57 Surgery 832–835 (Jun. 1965).

Wanpen Vongpatanasin, M.D. et al., *Prosthetic Heart Valves*, 335 N.E.J.M. 407–416 (Aug. 8, 1996).

Bruce F. Waller & Cass A. Pinkerton, *The Pathology of Interventional Coronary Artery Techniques and Devices*, in 1 Topol's Textbook Of Interventional Cardiology 449–476 (Eric J. Topol ed., 2nd ed. 1994).

Peter Whittaker, Ph.D. et al., *Transmural Channels Can Protect Ischemic Tissue*, 93 Circulation 143–1S2 (Jan. 1, 1996).

Currently pending and allowed claims in U.S. Patent application Ser. No. 09/055,488 filed Apr. 3, 1998.

Originally filed and currently pending claims in U.S. Patent application Ser. No. 09/054,815, filed Apr. 3, 1998.

"Percutaneous Transjugular Portosystemic Stent", Gerald Zemel et al., JAMA, vol. 266, No. 3, Jul. 17, 1991, pp. 390–393.

"Expandable Intrahepatic Portacaval Shunt Stents" Julio Palmaz et al., AJR:145, pp. 821–825, Oct. 1985.

"Expandable Intrahepatic Portacaval Shunt" Julio Palmaz et al., AJR:147, pp. 1251–1254, Dec. 1986.

"Transjugular Intrahepatic Portacaval Stent" Goetz M. Richter et al., Hepatic and Billard Radiology, pp. 1027–1030, vol. 174, Mar. 1990.

Robert J. Gardner, et al., *An Experimental Anatomic Study of Indirect Myocardial Revascularization*, Journal of Surgical Research, vol. 11, No. 5, pp. 243–247 (May 1971).

Ladislav Kuzela et al., *Experimental Evaluation of Direct Transventricular Revascularization*, Journal of Thoracic and Cardiovascular Surgery, vol. 57, No. 6, pp. 770–773 (Jun. 1969).

Banning G. Lary, MD, et al., *Myocardial Revascularization Experiments Using the Epicardium*, Archives of Surgery, vol. 98, No. 1, pp. 69–72 (Jan. 1969).

L. Levinsky, et al., *The Revival of the Horseshoe Graft*, The Thoracic and Cardiovascular Surgeon, vol. 27, No. 5 (Oct. 1979).

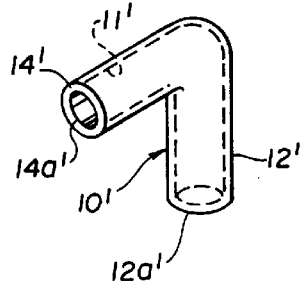
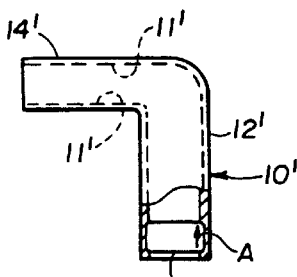
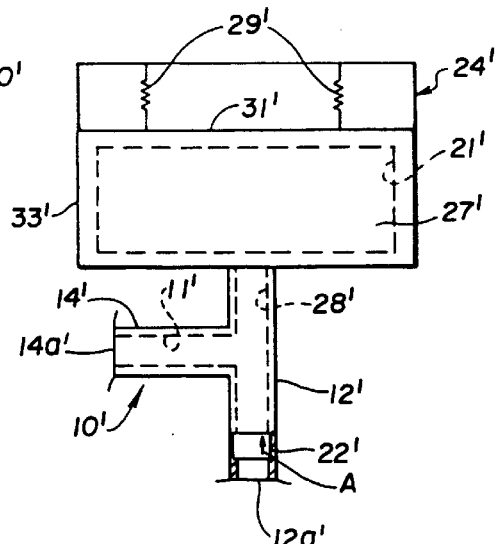
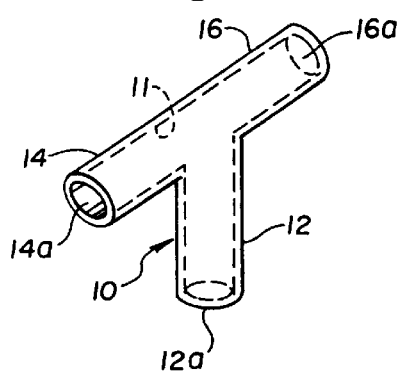
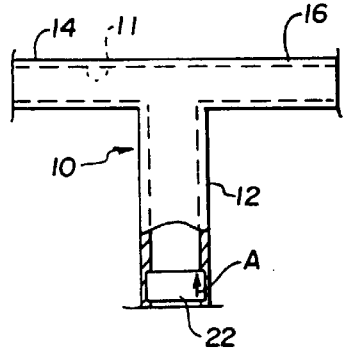
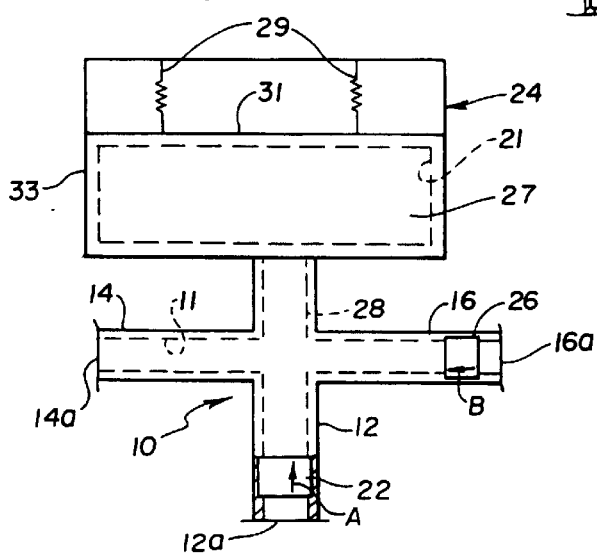

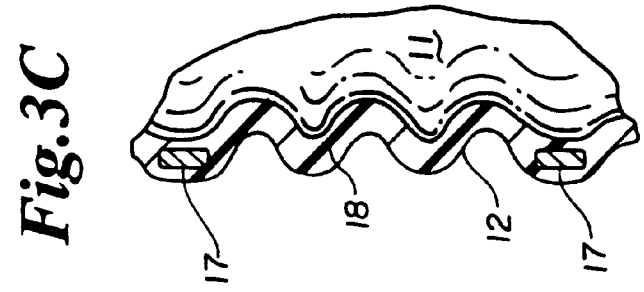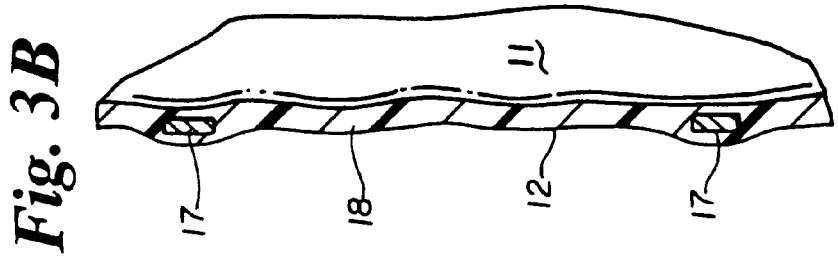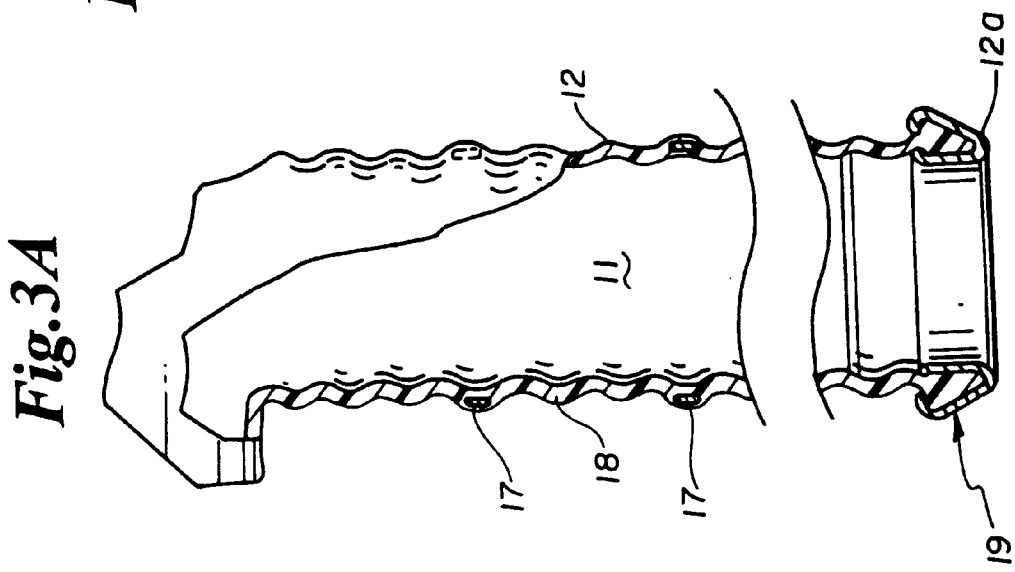

MESH TIP MYOCARDIAL IMPLANT

The present application is a continuation of U.S. patent application Ser. No. 09/055,488, filed Apr. 3, 1998, entitled CORONARY BYPASS IMPLANT now U.S. Pat. No. 6,093,166 and filed in the name of the same inventors as the present application, which is also a continuation of U.S. patent application Ser. No. 08/689,773, filed Aug. 13, 1996, entitled METHOD AND APPARATUS FOR PERFORMING CORONARY ARTERY BYPASS SURGERY, now U.S. Pat. No. 5,755,682 and filed in the name of the same inventors as the present application.

BACKGROUND OF THE INVENTION

1. Field of the Invention

The present invention relates generally to a method and apparatus for performing a coronary artery bypass procedure. More particularly, the present invention performs a coronary artery bypass utilizing a number of approaches including an open-chest approach (with and without cardiopulmonary bypass), a closed-chest approach under direct viewing and/or indirect thoracoscopic viewing (with and without cardiopulmonary bypass), and an internal approach through catheterization of the heart and a coronary arterial vasculature without direct or indirect viewing (with and without cardiopulmonary bypass).

2. Description of the Prior Art

Coronary artery disease is the leading cause of premature death in industrialized societies. But the mortality statistics tell only a portion of the story; many who survive face prolonged suffering and disability.

Arteriosclerosis is "a group of diseases characterized by thickening and loss of elasticity of arterial walls." DORLAND'S ILLUSTRATED MEDICAL DICTIONARY 137 (27th ed. 1988). Arteriosclerosis "comprises three distinct forms: atherosclerosis, Monckeberg's arteriosclerosis, and arteriosclerosis." Id.

Coronary artery disease has been treated by a number of means. Early in this century, the treatment for arteriosclerotic heart disease was largely limited to medical measures of symptomatic control. Evolving methods of diagnosis, coupled with improving techniques of post-operative support, now allow the precise localization of the blocked site or sites and either their surgical re-opening or bypass.

The re-opening of the stenosed or occluded site can be accomplished by several techniques. Angioplasty, the expansion of areas of narrowing of a blood vessel, is most often accomplished by the intravascular introduction of a balloon-equipped catheter. Inflation of the balloon causes mechanical compression of the arteriosclerotic plaque against the vessel wall. Alternative intravascular procedures to relieve vessel occlusion include atherectomy, which results in the physical desolution of plaque by a catheter equipped (e.g. a cutting blade or high-speed rotating tip). Any of these techniques may or may not be followed by the placement of mechanical support and called a "stent," which physically holds the artery open.

Angioplasty, and the other above-described techniques (although less invasive than coronary artery bypass grafting) are fraught with a correspondingly greater failure rate due to plaque reformation. Contemporary reports suggest re-stenosis is realized in as many as 25 to 55 percent of cases within 6 months of successful angioplasty. See Bojan Cercek et al., 68 AM. J. CARDIOL. 24C–33C (Nov. 4, 1991). It is presently believed stenting can reduce the re-stenosis rate.

A variety of approaches to delay or prevent re-blockage have accordingly evolved. One is to stent the site at the time of balloon angioplasty. Another is pyroplasty, where the balloon itself is heated during inflation. As these alternative techniques are relatively recent innovations, it is too early to tell just how successful they will be in the long term. However, because re-blockage necessitates the performance of another procedure, there has been renewed interest in the clearly longer-lasting bypass operations.

The current indications for coronary artery bypass grafting have been outlined. See LUDWIG K. VON SEGESSER, ARTERIAL GRAFTING FOR MYOCARDIAL REVASCULARIZATION: INDICATIONS, SURGICAL TECHNIQUES AND RESULTS 4–5 (1990). Criteria vary dependent upon whether the intent is therapeutic (that is, to reverse cardiac compromise in the patient currently suffering symptoms), or prophylactic (that is, to prevent a potentially fatal cardiac event from occurring in someone who is, at present, symptom free). Id.

The traditional open-chest procedure requires an incision of the skin anteriorly from nearly the neck to the navel, the sawing of the sternum in half longitudinally, and the spreading of the ribcage with a mechanical device to afford prolonged exposure of the heart cavity. If both lungs are deflated, a heart-lung, or cardiopulmonary bypass procedure, is also necessary.

Depending upon the degree and number of coronary vessel occlusions, a single, double, triple, or even greater number of bypass procedures may be necessary. Often each bypass is accomplished by the surgical formation of a seperate conduit from the aorta to the stenosed or obstructed coronary artery, at a location distal to the diseased site. A major obstacle has been the limited number of vessels that are available to serve as conduits. Potential conduits include the two saphenous veins of the lower extremities, the two internal thoracic arteries under the sternum, and the single gastroepiploic artery in the upper abdomen. Theoretically, if all of these vessels were utilized, the procedure would be limited to a quintuple (5-vessel) bypass. Because of this, newer procedures using a single vessel to bypass multiple sites have evolved. However, this technique is fraught with its own inherent hazards, though. When a single vessel is used to perform multiple bypasses, physical stress(e.g., torsion) on the conduit vessel can result. Such torsion is particularly detrimental when this vessel is an artery.

Unfortunately, attempts at using vessels from other species (xenografts), or other non-related humans (homografts) has been largely unsuccessful. See LUDWIG K. VON SEGESSER, ARTERIAL GRAFTING FOR MYOCARDIAL REVASCULARIZATION: INDICATIONS, SURGICAL TECHNIQUES AND RESULTS 38–39 (1990). Similarly, trials with synthetic alternatives have not been encouraging. See Id. at 39.

While experimental procedures transplanting alternative vessels continue to be performed, in general clinical practice there are five vessels available to use in this procedure over the life of a particular patient. Once these "spare" vessels have been sacrificed, there is little or nothing that modern medicine can offer. It is unquestionable that new methods, not limited by the availability of such conduit vessels, are needed.

In the past, the normal contractions of the heart have usually been stopped during suturing of the bypass vasculature. This can be accomplished by either electrical stimulation which induces ventricular fibrillation, or through the use of certain solutions, called cardioplegia, which chemically alter the electrolytic milleau surrounding cardiac muscles. Stoppage of the heart enhances visualization of the coronary vessels, while removing the need for blood flow through the coronary arteries during the procedure. This provides the surgeon with a "dry field" in which to operate and create a functional anastomosis. After the coronary artery bypass procedure is completed, cardioplegia is reversed, and the heart electrically stimulated if necessary. As the heart resumes the systemic pumping of blood, the cardiopulmonary bypass is gradually withdrawn. The seperated sternal sections are then re-joined, and the overlying skin and saphenous donor site or sites (if opened) are sutured closed.

The above-described procedure is highly traumatic. Immediate post-operative complications include infection, bleeding, renal failure, pulmonary edema and cardiac failure. The patient must remain intubated and under intensive post-operative care. Narcotic analgesia is necessary to alleviate the pain and discomfort.

The most troubling complication, once the immediate post-surgical period has passed, is bypass vessel re-occlusion. This has been a particular problem with bypass grafting of the left anterior descending coronary artery when the saphenous vein is employed. Grafting with the internal thoracic (internal mammary) artery results in long-term patency rate superior to saphenous vein grafts, particularly when the left anterior descending coronary artery is bypassed. Despite this finding, some cardiothoracic surgeons continue to utilize the saphenous vein because the internal thoracic artery is smaller in diameter and more fragile to manipulation; thus making the bypass more complex, time-consuming, and technically difficult. Additionally, there are physiological characteristics of an artery (such as a tendency to constrict) which increases the risk of irreversible damage to the heart during the immediate period of post-surgical recovery.

Once the patient leaves the hospital, it may take an additional five to ten weeks to recover completely. There is a prolonged period during which trauma to the sternum (such as that caused by an automobile accident) can be especially dangerous. The risk becomes even greater when the internal thoracic artery or arteries, which are principle suppliers of blood to the sternum, have been ligated and employed as bypass vessels.

Due to the invasive nature of the above technique, methods have been devised which employ contemporary thoracoscopic devices and specially-designed surgical tools to allow coronary artery bypass grafting by closed-chest techniques. While less invasive, all but the most recent closed-chest techniques still require cardiopulmonary bypass, and rely on direct viewing by the surgeon during vascular anastomoses. These methods require a very high level of surgical skill together with extensive training. In such situations, the suturing of the bypassing vessel to the coronary artery is performed through a space created in the low anterior chest wall by excising the cartilaginous portion of the left fourth rib. Also, as they continue to rely on the use of the patient's vessels as bypass conduits, the procedures remain limited as to the number of bypasses which can be performed. Because of these issues, these methods are not yet widely available.

In view of the above, it would be desirable to provide other methods or techniques by which adequate blood flow to the heart could be re-established which do not rely on the transposition of a patient's own arteries or veins. It would also be desirable to provide other methods or techniques by which adequate blood flow to the heart could be re-established which results in minimal tissue injury. It would be particularly desirable if such methods or techniques did not require opening of the chest by surgical incision of the overlying skin and the division of the sternum. It would be even more desirable if such methods or techniques did not require surgical removal of cartilage associated with the left fourth rib, did not require the surgical transection of one or both internal thoracic arteries, did not require the surgical incision of the skin overlying one or both lower extremities, and did not require the surgical transection and removal of one or both saphenous veins. It would also be desirable if such methods or techniques could be performed without stoppage of the heart, and without cardiopulmonary bypass.

The conventional surgical procedures (such as those described above) for coronary artery bypass grafting using saphenous vein or internal thoracic artery via an open-chest approach have been described and illustrated in detail. See generally Stuart W. Jamieson, Aortocoronary Saphenous Vein Bypass Grafting, in ROB & SMITH's OPERATIVE SURGERY: CARDIAC SURGERY, 454–470 (Stuart W. Jamieson & Norman E. Shumway eds., 4th ed. 1986); LUDWIG K. VON SEGESSER, ARTERIAL GRAFTING FOR MYOCARDIAL REVASCULARIZATION: INDICATIONS, SURGICAL TECHNIQUES AND RESULTS 48–80 (1990). Conventional cardiopulmonary bypass techniques are outlined in Mark W. Connolly & Robert A. Guyton, Cardiopulmonary Bypass Techniques, in HURST's THE HEART 2443–450 (Robert C. Schlant & R. Wayne Alexander eds., 8th ed. 1994). Coronary artery bypass grafting, utilizing open-chest techniques but without cardiopulmonary bypass, is described in Enio Buffolo et al., Coronary Artery Bypass Grafting Without Cardiopulmonary Bypass, 61 ANN. THORAC. SURG. 63–66 (1996).

Some less conventional techniques (such as those described above) are performed by only a limited number of appropriately skilled practitioners. Recently developed techniques by which to perform a coronary artery bypass graft utilizing thoracoscopy and minimally-invasive surgery, but with cardiopulmonary bypass, are described and illustrated in Sterman et al., U.S. Pat. Ser. No. 5,452,733 (1995). An even more recent coronary artery bypass procedure employing thoracoscopy and minimally-invasive surgery, but without cardiopulmonary bypass, is described and illustrated by Tea E. Acuff et al., Minimally Invasive Coronary Artery Bypass Grafting, 61 ANN. THORAC. SURG. 135–37 (1996).

Methods of catheterization of the coronary vasculature, techniques utilized in the performance of angioplasty and atherectomy, and the variety of stents in current clinical have been described and illustrated. See generally Bruce F. Waller & Cass A. Pinkerton, The Pathology of Interventional Coronary Artery Techniques and Devices, in 1 TOPOL's TEXTBOOK OF INTERACTIONAL CARDIOLOGY 449–476 (Eric J. Topol ed., 2nd ed. 1994) ; see also David W. M. Muller & Eric J. Topol, Overview of Coronary Athrectomy, in 1 TOPOL's TEXTBOOK OF INTERVENTIONAL CARDIOLOGY at 678–684; see also Ulrich Sigwart, An Overview of Intravascular Stents: Old & New, in 2 TOPOL's TEXTBOOK OF INTERVENTIONAL CARDIOLOGY at 803–815.

Finally, some techniques remain in the experimental stages, and are limited to animal testing. Direct laser canalization of cardiac musculature (as opposed to canalization of coronary artery feeding the cardiac musculature) is described in Peter Whittaker et al., Transmural Channels Can Protect Ischemic Tissue: Assessment of Long-term Myocardial Response to Laser- and Needle-Made Channels, 94(1) CIRCULATION 143–152 (Jan. 1, 1996).

SUMMARY OF THE INVENTION

According to the present invention, a method and apparatus for surgically bypassing an obstructed coronary artery or arteries relies on the establishment of a channel or channels leading directly from a chamber of the heart into the obstructed coronary artery or arteries at a site or sites distal to the obstruction. At the time of, or prior to the procedure, coronary arterial obstruction can be identified through angiography. Standard angiographic techniques utilize radio-opaque dyes introduced into the coronary arterial vasculature to identify defects in blood flow by standard radiological techniques. Standard radiological techniques involve visualization of flow defects through the taking of X-rays or viewing under fluoroscopy at the time that a radio-opaque dye is injected. Alternatively, a video recording system may be enlisted to record these fluoroscopic images, and allow the identification of more subtle defects through repeated viewings. At the time of, or prior to the procedure, a site or sites for the coronary artery bypass procedure can thus be selected.

The present invention is particularly useful for coronary artery bypass procedures in a patient suffering from obstructive coronary artery disease. The methods can be performed while the patient is anesthetized. Anesthesia may be, but is not limited to, general anesthesia. The present permits an array of procedures of varying invasiveness. As in other procedures, the level of anesthesia necessary is expected to vary directly with the invasiveness of the surgery. The present invention, because it minimizes normal tissue damage, is especially useful for coronary artery bypassing in a patient who, because of other medical problems such as chronic respiratory failure, must be maintained at a higher level of consciousness than that usually realized during standard general anesthesia. In such a patient, a less invasive approach may be chosen. As in any major surgical procedure, the patient's heart and respiratory rates, peripheral oxygenation, urinary output, and other bodily functions may be monitored. During some or all of the bypass, cardiac contractions can be slowed, or stopped, to both improve visualization of the coronary vasculature, and to reduce the oxygen requirements of cardiac muscle. An intra-esophageal probe or probes, or other appropriately-placed probe or probes to monitor the cardiac cycle, and to trigger power to the intraventricular laser when utilized, may be advantageous.

The present invention can be performed in an operating room equipped with standard X-ray, and/or fluoroscopy, and/or cine-fluoroscopy equipment, as is standardly utilized during cardiac catheterization procedures. The present invention can be performed while the treating physician or physicians view the X-rays, and/or fluoroscopic images produced during the procedure, as is standardly done during cardiac catheterization.

The present invention avoids the previous limitations on the number of performable bypass procedures. Due to the limited number of arteries and/or veins available, standard procedures become increasingly risky to repeat. Rather than relying on harvested veins and arteries as bypass conduits, the present invention forms a channel (or conduit) which leads directly from a chamber of a patient's heart into a coronary artery at a site distal to the obstruction or narrowing.

In the most preferred embodiment, the left ventricle is the chamber of the heart utilized. There are two reasons for this selection. First, the left ventricle normally provids blood to the coronary arteries, because it pumps blood into the aorta from which the coronary arteries branch. Therefore, the blood pressure peak generated by the left ventricle is most similar to the blood pressure peak the proximal coronary artery would normally experience. Second, the blood which flows into the left ventricle is returning from the the lungs. In the lungs the blood acquires oxygen and loses carbon dioxide. Thus, the blood available by shunting from the chambers of the left side of the heart will have a higher oxygen and lower carbon dioxide content then that blood within the right-sided heart chambers.

The Open-Chest Procedure

As a first step, the patient can be prepared in the usual fashion for open-chest cardiac bypass surgery. Once access to the heart and coronary vasculature is gained, cardiopulmonary bypass and stoppage of the heart may, but is not necessarily, performed.

As a second step, blood flow through the coronary artery to be bypassed is stopped. One example by which blood flow can be stopped is by clamping the artery proximal to the chosen bypass site. Another example by which blood flow can be discontinued is by forming a loop around the artery with suture and applying traction.

As a third step, an incision is formed in the artery at a site distal to the narrowing or obstruction. A channel is then formed leading from a coronary artery through the wall of the coronary artery, through the underlying cardiac muscle and into a chamber of a heart. One example by which such a channel could be formed is by laser ablation of the intervening tissue, another example is by forming an incision with an electrosurgical tool which will simultaneously cut and cauterize the intervening tissue, and yet another example is by blunt dissection with an appropriate blunt tool such as an awl punch or trocar.

As a fourth step, one arm of an appropriately dimensioned apparatus of the present invention is inserted through this channel leading into the chamber of the heart. The remaining arm or arms of the apparatus are then seated within the lumen of the coronary artery.

Depending on the relationship over time of the pressures present within the chamber of the heart as compared to the pressures realized within the coronary artery at the bypass location, a check valve permitting unidirectional blood flow from the chamber of the heart into the coronary artery may be associated with the apparatus. The use of a check valve, and the opening pressure of such a valve when employed, can be individually determined through selective catheterization of the coronary artery and the chamber of the heart either prior to, or at the time of, the bypass procedure. See Minoru Hongo et al., Effects of Heart Rate on Phasic Coronary Blood Flow Pattern and Flow Reserve in Patients with Normal Coronary Arteries: A study with an Intravascular Doppler Catheter and Spectral Analysis, 127(3) AM. HEART J. 545–51 (March 1994) (outlining newer techniques by which pressures within the coronary artery can be measured during the normal cardiac cycle). Simultaneous electrocardiography may also be useful in this regard. Such catheterization and blood pressure measurements performed in concert with stress testing and electrocardiography can be utilized to determine what minimal pressures are necessary within the bypassed coronary artery to produce adequate blood flow at rest and during stress. Correlation of the pressure necessary within the coronary artery to that present within the chambers of the heart can be used to establish the appropriate chamber of the heart to utilize. In the most preferred embodiment, the left ventricle is anticipated.

As a fifth step, the coronary artery incision is closed in the usual fashion. One example of closure is re-approximating the walls of the coronary artery with suture, while another example is closure of the walls by staples which interlock with the underlying device of the present invention.

As a sixth step (if needed), cardiac contractions are reinitiated. One example by which cardiac contractions are commonly reinitiated is through electrical defibrillation, while another example is through the reversal of cardioplegia by standard techniques. Cardioipulmonary bypass, if utilized, can then be slowly discontinued.

As a seventh step, the pericardium, sternum, and overlying skin can then be re-approximated and sutured and/or stapled closed, as is standardly performed following open-chest surgery.

The Closed-Chest Procedure

In another embodiment, the method and apparatus of the present invention reduces trauma to normal tissue, limits blood loss, and lowers the risk of infection heretofore associated with standard coronary artery bypass procedures. In this embodiment, the procedure is performed under direct and indirect viewing through a space (i.e., window) formed in the left anterior chest wall, as well as viewed through a thoracoscope. In this embodiment, the surgery is performed through the formed window via a series of access trocar sheaths, which allow the introduction of surgical instruments. See Sterman et al., U.S. Pat. No. 5,452,733 (1995). See, also Acuff et al., Minimally Invasive Coronary Artery Bypass Grafting, 61 ANN. THORAC. SURG. 135–37 (1996). The basic steps of the procedure are similar to the open-chest technique outlined above. The location of the bypass site, the requirement for adequate visualization, and the overall health of the particular patient are factors likely to contribute to the decision as to which procedure to employ.

The Catheterization Procedure

The method and apparatus of the present invention, in yet another embodiment, greatly minimizes damage to normal tissue, although at the expense of the (at least partial) loss of direct visualization, by performing the coronary bypass surgery via catheterization. In this embodiment, the entire procedure is limited to two incisions: one in the groin and one in the right superior-anterior chest. Catheter access to the coronary arterial vasculature and chambers of the heart are achieved through these incisions.

As a first step, the obstructed coronary artery is catheterized by introduction of a catheter into the innominate or femoral artery and by the feeding of the catheter retrograde through the ascending aorta and into the obstructed artery via standard catheterization techniques. If the obstruction does not allow passage of the catheter past the site or sites of obstruction, the catheter can be removed, and angioplasty, atherectomy, or another appropriate procedure can be performed. Once the catheter is positioned distally to the site of the obstruction, a stent is secured to the arterial wall at the preselected bypass site. This can be accomplished by inflation of a balloon circumferentially attached to the catheter. This stent provides the appropriate structural strength to ensure continued integrity of the coronary artery, following opening of the coronary arterial wall. Once this stent has been placed, the catheter is withdrawn and allowed to rest within the ascending aorta.

As a second step, a chamber of a heart is catheterized. The left side of the heart, including the left auricle and left ventricle, can be catheterized by introduction of a penetration means (e.g., laser or radiofrequency) equipped catheter into the innominate or femoral artery and by the feeding of said catheter retrograde through the ascending aorta and into said left auricle or left ventricle via standard catheterization techniques. In the preferred embodiment, the left ventricle is catheterized in this manner. In one embodiment, a channel, leading from one of the chambers of the left side of a heart and continuing through the deep arterial wall of a coronary artery, at a site consistent with the previously-placed intracoronary stent, is created by laser or radiofrequency ablation, or like techniques, while being viewed through standard radiologic techniques. Once this channel appears to have been created, radio-opaque dye can be injected into the channel via a port on the intraventricular catheter. Once this radio-opaque dye, visualized by standard angiographic techniques, is seen to flow into the coronary artery at the chosen bypass site, ablation or like techniques of the heart chamber wall is discontinued.

As a third step, the catheter, which is at rest within the ascending aorta, is re-inserted into the coronary artery and advanced under standard radiologic visualization until it is again located at the site of the previously-placed intracoronary stent. The balloon on the tip of the catheter is then re-inflated. The inflation of this balloon serves two purposes. First, in the case where there is no cardiopulmonary bypass, the inflation of this catheter prevents blood from flowing from the coronary artery, through the channel formed in the second step described above, and into a chamber of the heart. To facilitate the supply of blood to the microcirculation normally fed by the coronary artery being bypassed, there are channels within the proximal and distal aspects of the intracoronary catheter. These channels allow blood within the coronary artery to enter the catheter upstream from the balloon and to flow within the catheter downstream and exit from the catheter through channels located within the catheter but distal to the balloon. The second function served by inflation of this balloon is as a physical stop for the intraventricular catheter located within the formed channel, as outlined below.

As a fourth step, the intraventricular catheter is advanced to come to rest against the wall of the inflated balloon located on the tip of the intracoronary catheter. A balloon located on the distal tip of the intraventricular catheter is then inflated. Inflation of this balloon results in the seating of a an apparatus which circumferentially surrounds this balloon against the walls of the formed channel. In one embodiment, this device can be a spiral sheet. In this embodiment, inflation of the balloon of the intraventricular catheter results in this spiral sheet being forced into an expanded position; where it takes the form of a hollow tube. In this embodiment, once this spiral sheet is forced into the form of a hollow tube, an interlocking lip on this device results in the locking of the former spiral sheet into a hollow tube configuration. In another embodiment, the expansion of the balloon on the tip of the intraventricular catheter results not only in the apparatus seating against the walls of the formed channel, it also results in the interlocking of the apparatus with the intracoronary stent previously placed. In either embodiment, the proper positioning of the intraventricular catheter tip to facilitate proper positioning of the device within the formed channel, and to result in the interlocking with the intracoronary stent if chosen, can be determined by standard radiologic techniques prior to the inflation of the intraventricular balloon. Once the device is properly postitioned and locked within the formed channel, the balloon on the tip of the intraventricular catheter is deflated. The intraventricular catheter is then withdrawn from the body.

As a fifth step, a third catheter is inserted into the innominate or femoral artery and fed retrograde through the ascending aorta and into a chamber of the left side of the heart via standard catheterization techniques. In a preferred embodiment, the third catheter is advanced into the left ventricle.

The distal tip of this third catheter holds an apparatus which has the ability to be mechanically interlocked with the first apparatus which was placed within the formed channel in the fourth step described above. The second apparatus is place within the lumen of the fromed channel through manipulation of the intraventricular catheter by standard catheter-control techniques.

In one embodiment the second apparatus can be secured to the walls of the channel itself through stapling, biologically-effective glueing, or the like. In another embodiment, this second apparatus can be interlocked with the first apparatus previously placed through various conventional techniques by which one hollow tube is mechanically locked to another hollow tube. In one embodiment, this interlocking could take the form of threading. In another embodiment, this interlocking could be accomplished by a tongue on the second apparatus that slips into a groove on the first apparatus.

The second apparatus allows blood to flow within the lumen of the apparatus either bidirectionally, or unidirectionally. In one embodiment, the second apparatus can be equipped with a check valve which allows blood to flow from a chamber of a heart into a coronary artery, while prohibiting blood flow in the opposite direction. In this embodiment, this flow-restrictive apparatus is placed within the laser-ablated channel and associated with the previously-placed apparatus.

Once the second apparatus has been located within the formed channel, and either effectively secured to the channel walls, or effectively secured to the first apparatus, the second apparatus can be released from the tip of the third catheter. In one embodiment, proper interlocking of the second apparatus to the first apparatus can be ascertained by standard radiographic techniques. In another embodiment, proper interlocking of the second apparatus to the first apparatus can be indirectly viewed through a remote fiberoptic viewing system, or the like, inherent to the third catheter. The third catheter is then withdrawn from the body.

As a sixth step, blood flow from a chamber of the heart into the bypassed coronary artery and, in cases where a check valve has been placed, the corresponding absence of flow from the coronary artery into a chamber of the heart, can be determined by standard angiographic techniques.

Clarification of Meanings

Living biological organisms react in a range of varying ways to foreign materials. The term foreign materials is meant to include all materials, whether biological or non-biological, which are not normally present within that particular subject.

Because subjects respond to foreign materials in a range of various ways, the apparatus of the present invention can be exposed to cells, treated by biological compounds, or exposed to pharmaceutical or other chemical agents, which reduce the reactions normally resulting when foreign bodies are internally introduced.

With regard to the specification and claims of this application, the phrase "reduce reaction" is meant to indicate a reduction in tissue responses. This is meant to include, but not to be limited to, immune reactions, tissue scarring, blood clotting, and the like. The literature is replete with pharmaceuticals which can be either locally or systemically administered and which decrease the immune response to foreign bodies. These include corticosteroids, and the like. It is also well known in the literature that there are pharmaceutical agents which reduce scar tissue formation following injury. Newer published techniques to reduce re-stenosis in transplanted artificial vessels include coating such devices with non-immunogenic endothelial cells or fibroblasts. A common problem with transplanted vessels is blood clotting, and agents which reduce such clotting have been widely reported.

The phrase "reduce reaction" is also meant to indicate a reduction in the changes in arterial walls associated with the family of diseases known as arteriosclerosis. Arteriosclerosis is the most common cause of coronary artery occlusion and/or narrowing. Pharmaceutical agents which inhibit the formation of arteriosclerotic plaques have been discovered. Coating the device with agents which decrease the accumulation of such deposits can be beneficial in the prevention of re-stenosis.

Conclusion

In summary, creating a channel or channels which lead directly from a chamber of the heart into the coronary arterial vasculature should decrease the morbidity and mortality of bypass surgery, should reduce post-surgical recovery time, should decrease coronary artery bypass grafting costs, and should allow the creation of multiple bypass sites to multiple diseased coronary arteries either simultaneously, or at some later point in time. In no way is the procedure limited by the availability and patency of veins or arteries harvested from the bypass patient. In addition, the invention eliminates the risk of aneurysmal dilitation and subsequent functional deterioration of transplanted saphenous veins, as well as the risk of arterial constriction and subsequent functional deterioration of internal thoracic or gastroepiploic arteries, particularly when compared to techniques which result in torsion on transplanted artery.

BRIEF DESCRIPTION OF THE DRAWINGS

FIG. 1A is a right anterior superior perspective view of an L-shaped apparatus for use in the present invention.

FIG. 1B is a side elevation view of the apparatus of FIG. 1A shown partially in section to reveal an optional check valve located in the lumen of the anchor arm of the apparatus.

FIG. 1C is a side elevation view of a apparatus similar to that of FIG. 1A showing the addition of a capacitance pressure reservoir as an alternative embodiment.

FIG. 2A is a right anterior superior perspective view of a T-shaped apparatus for use in the present invention.

FIG. 2B is a side elevation view of the tube of FIG. 2A shown partially in section to reveal an optional check valve located in the lumen of the anchor arm of the apparatus.

FIG. 2C is a side elevation view of the tube of FIG. 2A shown partially in section to reveal one optional check valve located in the lumen of the anchor arm of the apparatus, and another optional check valve located in one of the intracoronary arms of the apparatus.

FIG. 2D is a side elevation view of a apparatus similar to that of FIG. 2A showing the addition of a capacitance pressure reservoir as an alternative embodiment.

FIG. 3A is a partial side elevation view of an apparatus similar to that of FIGS. 1A and 2A shown partially in section to reveal a flexible anchor arm with rigid rings ensheathed in a flexible covering as an alternative embodiment.

FIG. 3B is a partial side elevation view of an apparatus similar to that of FIG. 3A shown in section in an extended form.

FIG. 3C is is a partial side elevation view of an apparatus similar to that of FIG. 3A shown in section in a compressed form.

DESCRIPTION OF PREFERRED EMBODIMENT

A. The Problem

Figure 4:
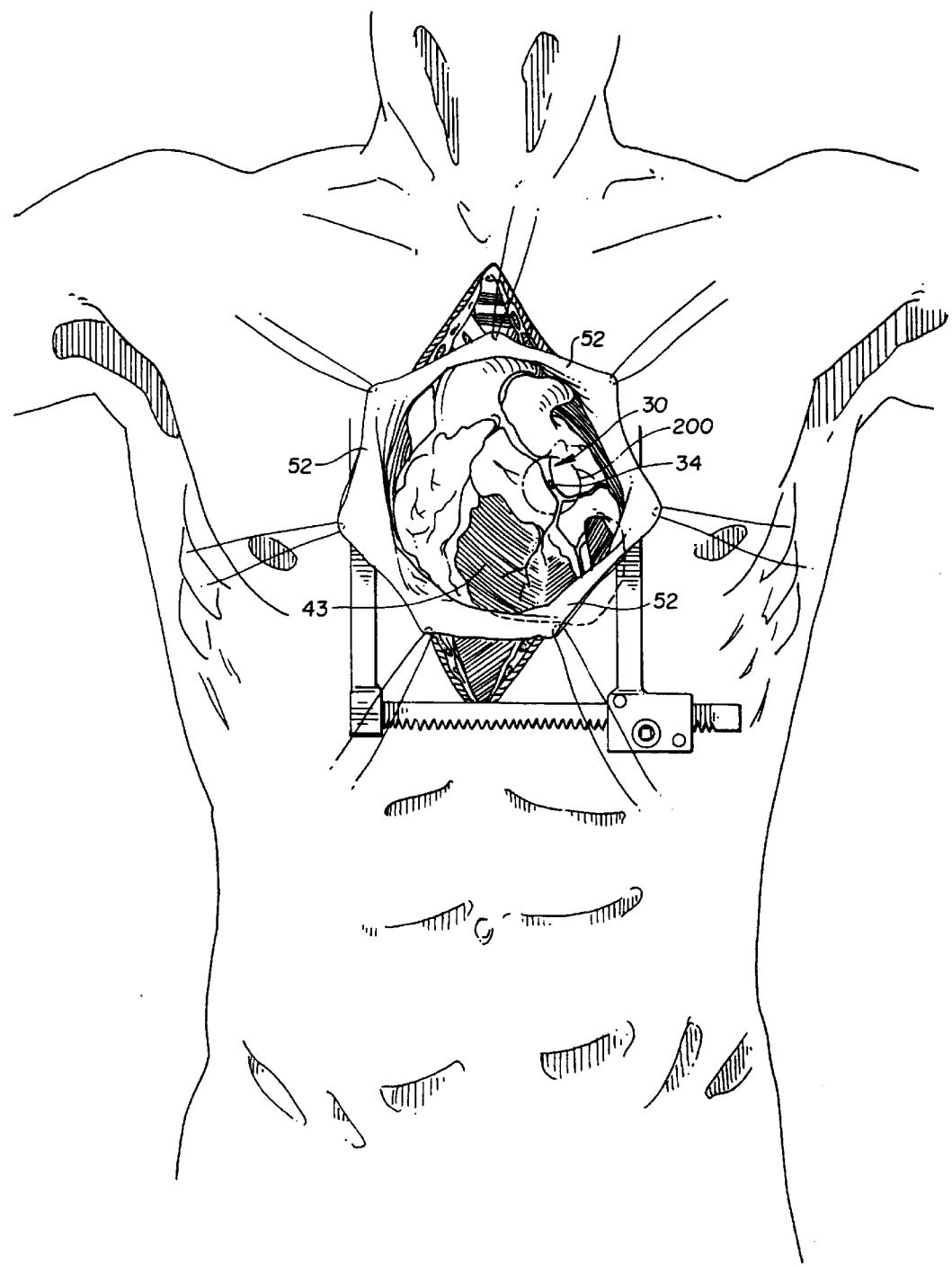
FIG. 4 is an anterior view of a human chest which is incised longitudinally to reveal a dissected pericardium, and mediastinal contents.

Heart disease remains the leading cause of death in the industrialized world. Myocardial infarction, or irreversible damage to cardiac muscle, can result when cardiac musculature is inadequately oxygenated for a sufficient period of time. The leading cause of inadequate oxygenation is insufficient blood flow through the coronary arteries which perfuse the cardiac musculature. The most common cause of insufficient blood flow within the coronary arteries is vascular stenosis or occlusion. By far the leading cause of stenosis or occlusion of the coronary arteries is arteriosclerosis.

Blockage of the coronary vasculature may be reversed by several means. The most durable solution to the problem, though, is coronary artery bypass grafting.

Traditionally, the bypass procedure has entailed forming a new pathway where blood from the aorta is supplied to coronary artery or arteries at a site or sites distal to the obstruction. It is axiomatic that this form of coronary artery bypass grafting is possible only where suitable conduits are available for transplantation. In general, vessels harvested from other species (xenografts), as well as those taken from unrelated subjects of the same species (homografts), have proven insufficiently durable as transplant conduits. Similarly, transplants with artificial vessels have been largely unsuccessful. Therefore, coronary artery bypass grafting has been available only to those subjects who posess suitable transplant vessels, and who are physically able to withstand the harvesting and transplantation of one or more of these vessels across their coronary vasculature.

B. The Invention

The invention departs from the traditional bypass approach. Rather then providing an alternative pathway for blood to flow from an aorta to a coronary artery, the invention provides a blood flow path leading directly from a chamber of a heart to a coronary artery, at a site downstream from the stenosis or occlusion. The surgical placement of the apparatus of the present invention establishes this alternative pathway.

C. Embodiments with the Open Chest Approach

1. The Apparatus of the Present Invention for Use in the Open Chest Approach As will be more fully described, the present invention places an apparatus for defining a blood flow conduit directly from a chamber of a heart to a coronary artery downstream of an occluded site. Before describing the surgical methods for placing such an apparatus, an apparatus of the present invention will be described. The purpose of the following description is to clarify an understanding of the novel surgical procedures using such an apparatus.

The apparatus of the present invention can be a variety of shapes or sizes, and is not meant to be limited as to size, shape, construction, material, or in any other way by the following examples in which a prefered embodiment is illustrated.

With initial reference to FIGS. 2A, 2B, 2C, 2D and 2E, an embodiment of an apparatus according to the present invention is shown as a T-shaped stent 10. The stent 10 is hollow, and includes two axially-aligned intracoronary arms 14, 16 terminating at open ends 14a, 16a. An anchor arm 12 (having an open end 12a) extends perpendicularly to arms 14, 16. The entire stent 10 is hollow to define a blood flow conduit 11 providing blood flow communication between open ends 12a, 14a and 16a.

As will be more fully discussed, arms 14 and 16 are adapted to be placed and retained within a lumen of a coronary artery on a downstream side of an occlusion with open ends 14a, 16a in blood flow communication with the lumen. The anchor arm 12 is adapted to extend through and be retained in a heart wall (e.g., a wall of the left ventricle) with the open end 12a in blood flow communication with blood within the chamber. Accordingly, when so placed, the stent 10 defines a surgically-placed conduit establishing direct blood flow from the heart chamber to the artery. By "direct" it is meant that the blood flow does not pass through the aorta as occurs in traditional bypass procedures.

FIG. 2B illustrates use of an optional check valve 22 within the stent 10 and positioned in anchor arm 12. Check valves are well known and valve 22 permits flow only in the direction of arrow A (i.e., from open end 12a to open ends 14a, 16a) while blocking reverse flow. Valve 22 is used to prevent the back-flow of blood from the coronary artery to the heart chamber. Valves sufficiently small to fit into arm 20 are within the skill of the art. For example, Wanpen Vongpatanasin et. al, Prosthetic Heart Valves, 335(6) N.E.J.M. 407–416 (Aug. 8, 1996) describes valves of 24 square millimeters.

FIG. 2C illustrates the use of check valve 22 as well as a second check valve 26 in arm 16 near the open end 16a of the apparatus. The second check valve 26 permits blood flow only in the direction of arrow B. Valve 26 is used to prevent the back flow of blood in an upstream diretion within the coronary artery. For example, the coronary artery may not be completely obstructed and may have a reduced flow past an obstruction. The use of the T-stent 10 with axially alligned arms 14, 16 takes advantage of such reduced flow and supplements such flow with blood through anchor arm 12. As will be described, the stent 10 is placed with the arms 14, 16 in the lumen of the artery with opening 16a positioned on the upstream side (i.e., nearest to, but still downstream of, the obstruction). Thus, valve 26 permits the utilization of normal blood flow while blocking back-flow.

While a T-shaped stent 10 is presently anticipated as most desirable, an L-shaped stent 10' (FIGS. 1A, 1B, 1C) may be used to completely bypass the coronary obstruction. An L-shaped stent 10' has an anchor arm 12' with an open end 12a'. Unlike stent 10, stent 10' has only one intracoronary arm 14' perpendicular to arm 12'. Arm 14' has an open end 14a' and stent 10' is hollow to define a continuous fluid pathway or conduit 11' from end 12a' to end 14a'. In application, arm 14' is placed within the lumen of an artery. End 14a' faces downstream from an obstruction. Arm 12' is placed through the heart wall with end 12a' in fluid communication with blood within the heart chamber. As illustrated in FIG. 1B, the anchor arm 12' can include a check valve 22' similar to valve 22 of stent 10.

Stent 10, 10' may be rigid, or have varying flexibilities. FIGS. 3A, 3B and 3C demonstrate one embodiment where the anchor arm (i.e., elements 12, 12' of FIGS. 1A and 2A) is comprised of a number of rings 17 surrounded by a membrane 18. In FIGS. 3A–3C, only anchor arm 20 is shown. It will be appreciated that anchor arm 20' may be identically constructed. In the embodiment of FIGS. 3A–3C, the rings 17 can be constructed of teflon, and the surrounding membrane 18 can be constructed of a double-walled dacron sheath into which the teflon rings 17 are sewn. In this embodiment, the rings 17 provide structural strength. The structural strength maintains an open lumen or conduit 11 leading into the coronary artery by preventing the conduit 11 from collapsing by reason of contraction of the heart muscle surrounding the anchor arm 12. The series of rings 17 provide a degree of flexibility which allows a channel formed through the heart chamber muscular wall (receiving anchor arm 12) to be angled or curved. In addition, the flexability of the surrounding sheath 18 in concert with the rigid rings 17 will allow the anchor arm 12 to expand, FIG. 3B, and contract, FIG. 3C, with the contractions and relaxations of the surrounding cardiac musculature.

It should be noted that, because of the semi-rigid nature of the anchor arm 12 constructed in this manner, a method of attaching that end of the anchor arm in contact with the inner surface of a chamber of a heart can be useful. In the example illustrated, this attaching mechanism 19 is a rigid teflon flange. It will be appreciated that other mechanisms of attachment, such as suturing, biologically glueing, etc. are alternative options.

The apparatus of the present invention (as thus described) provides a path 11 through which blood flows from a chamber of a heart and into a coronary artery. Additionally, such a device can store blood under pressure for a period of time prior to its introduction into a coronary artery. As depicted in the embodiments of FIGS. 1C and 2D, this aspect of the apparatus 10, 10' of the present invention is referred to as a capacitance pressure reservoir (CPR) 24, 24'.

It is well known from the literature that blood flow through the normal coronary artery is cyclical. Blood flow is increased during diastole (when the heart muscle is in a relaxing state), and decreases or reverses during systole (when the heart muscle is in a contracting state). See, e.g., F. Kajiya et al., Velocity Profiles and Phasic Flow Patterns in the Non-Stenotic Human Left Anterior Descending Coronary Artery during Cardiac Surgery, 27 CARDIOVASCULAR RES. 845–50 (1993).

The pressure gradient across the lumens 12a, 12a', 14a', 16a of the apparatus 10, 10' of the present invention will vary over the cardiac cycle. For example, during systole, the contraction of the heart muscles will generate high relative pressures within the left ventricle. The pressures within the coronary arterioles and capillaries distal to the bypass site are also high during this time, due to the external compression of the contracting cardiac musculature surrounding these vessels. This is particularly true for the vessels of the microcirculation deep within the heart which serve the endocardium. The optional CPR 24, 24' stores the pressurized blood during systole for delivery to the heart muscles via the coronary circulation during diastole when pressures are reduced. In essence, the CPR 24, 24' serves a function similar to the elastic connective tissue of the thick-walled aorta. The necessary function of the CPR 24, 24' is to store blood under higher pressure, and to later provide that stored blood to the microcirculation when the external pressures on that microcirculation are reduced.

As depicted in FIGS. 1C and 2D the check valves 22, 22' n limits blood flow in the direction of A, which is from a chamber of a heart into the apparatus 10, 10' via the lumen 11, 11'. The pressure on the blood within the chamber of a heart will be greatest when the surrounding cardiac musculature is in the contracting phase of the cardiac cycle. Because it is during this phase of the cardiac cycle that the external pressure on the coronary artery microcirculation is also highest, blood flow through the lumen 11, 11' of the apparatus 10, 10' could be limited. To counteract this tendency, the device 10, 10' is equipped with a reservoir 24, 24' which stores this pressurized blood flowing from a chamber of the heart during the cardiac contraction.

The reservoir, or CPR 24, 24' is schematically illustrated in FIGS. 1C, 2D. It can be appreciated that the stent 10, 10' is provided with a fluid passage 28, 28' in communication with conduit 11, 11'. The passage 28, 28' communicates with an expandable volume (or storage chamber) 27, 27' defined by a movable wall 31, 31' contained within a fixed housing 33, 33'. Springs 29, 29' between wall 31, 31' and housing 33, 33' urge the wall 31, 31' to move to reduce the size of volume 27, 27'. The springs 29, 29' are pre-loaded to exert a force on wall 31, 31' n less than a force exerted by blood within volume 27, 27' during the contraction phase of the cardiac cycle, but greater than the force exerted by blood within volume 27, 27' during the relaxation phase of the cardiac cycle.

The apparatus 10, 10' is constructed in a manner which allows blood to flow into the storage chamber 27, 27' of the apparatus 10, 10' through the lumen 11, 11' of arm 28, 28' of the apparatus when the cardiac musculature is contracting. When blood is flowing into the storage chamber 27, 27', the kinetic energy of the flowing blood is converted to potential energy, and stored in 29, 29'. During the relaxation phase of the cardiac musculature, the potential energy stored in 29, 29' of the CPR 24, 24' is then re-converted to kinetic energy in the form of blood flow out of the storage chamber 27, 27' of the apparatus 10, 10' via the lumen 11, 11' of arm 28, 28' of the apparatus.

While the CPR 24, 24' is illustrated with a movable wall 31, 31' and springs 29, 29' to define a variable volume, other designs can be used. For example, the CPR 24, 24' can be a balloon-like structure. As it fills with blood, the pressure on that blood increases through the stretching of an elastic component of a balloon. In another embodiment, the CPR, 24, 24', can be a hollow bag, made of a material which is inelastic, but impermeable to liquids, and pliable similar to a plastic bag. When the heart contracts, blood is forced through lumen 11, 11' n of arm 28, 28' of the apparatus 10, 10' of the invention into the collection bag. In this embodiment, the CPR, 24, 24', is physically located in the potential space existing between the fibrous and serous layers of the pericardium. When the heart expands during the relaxation phase of the cardiac cycle, the increasing heart size within the fixed pericardial sac results in increasing external pressure on this collection bag. This increasing external pressure would then force blood to flow from the collection bag and back through the lumen 11' 11' of arm 28, 28' of the device 10, 10'. The incorporation of a check valve 22, 22' within the anchoring arm 12, 12' of the device 10, 10' would limit the flow of blood out of the device during diastole to the coronary artery via the lumen 11' 11' of arms 14a, 14a', 16a of the device, of the apparatus 10, 10'. Similarly, the incorporation of the check valve 26 within the intracoronary arm 16 of the T-shaped apparatus 10, when employed with the check valve 22 within the anchor arm 20 of the device 10, would limit the flow of blood out of the device during diastole to the portion of the coronary artery distal to the bypass site via the downstream lumen 11 of arm 14a.

The inner and outer cross-sectional diameters of a coronary artery decreases with the distance from the arterial origin. Eventually, the artery branches into a number of arterioles, which feed the capillary bed of the coronary arterial microcirculation.

The typical diameter of a lumen of a coronary artery is, in general, species specific; increasing with heart size. In humans, this lumen diameter is dependent upon which artery is being evaluated, but usually ranges from 2.5 to 4 mm in diameter, and decreases with distance from the aortic origin. In the preferred embodiment, the cross-sectional outer diameter of the intracoronary arms 14, 14', 16 of the device of the present invention should effectively approximate the diameter of the lumen of the coronary artery being bypassed, at the bypass site. This allows the complete re-approximation of the previously opened superficial wall of the coronary artery during surgical closure, without high suture or staple tension resulting. In the most preferred embodiment, the outer diameter of the intracoronary arms 14, 14', 16 of the device 10, 10' of the present invention is equal to the diameter of the lumen of the coronary artery which is being bypassed, at the bypass location. When a CPR is placed, the artery wall may need to be expanded by the addition of a patch, such as dacron, well known in the art.

Also, due to smooth muscle relaxation and secondary vascular dilitation, the cross-sectional diameter of a lumen of a coronary artery will increase with the oxygen demand of cardiac muscle during times of stress. The cross-sectional inner diameter of the intracoronary arms 14, 14', 16 of the device 10, 10' of the present invention should effectively approximate that diameter necessary to provide adequate blood flow through the downstream lumen of the device 14a, 14a' to effectively oxygenate the cardiac musculature normally supplied by the microcirculation of the coronary artery. In the preferred embodiment, the cross-sectional inner diameter of the intracoronary arms 14, 14', 16 of the device 10, 10' of the present invention should effectively approximate that diameter necessary to provide adequate blood flow through the lumen of the device to effectively oxygenate the cardiac musculature normally supplied by the microcirculation of the coronary artery during both times of cardiovascular resting and stress.

Prior to bypass surgery, an initial approximation of the required cross-sectional outer diameter of the intracoronary arms 14, 14', 16 of the apparatus 10, 10' of the present invention can be gained by standard radiographic techniques. Also, prior to bypass surgery, the appropriate opening pressure of a check valve 22, 22' of the apparatus 10, 10' of the present invention can be determined by the dynamic measurements of coronary artery pressure, blood flow, and heart chamber pressures through selective catheterization with standard techniques. See Minoru Hongo et al., 127(3) AM. HEART J. 545–51 (March. 1994).

During the coronary artery bypass procedure, the most appropriate sizing of the intracoronary arms 14, 14', 16 of the device 10, 10' of the present invention can be re-assessed. This can be accomplished by probing the distal and proximal aspects of the coronary artery at the chosen bypass site with blunt instruments of known outer diameters. Such sizing by probes is well-known in the literature. To facilitate the effective matching of the external diameter of the intracoronary arms 14, 14', 16 of the device 10, 10' of the present invention to the lumen 34 of the coronary artery to be bypassed, an assortment of devices of the present invention of various diameters can be available for the surgeon to select from.

2. The Method of the Present Invention Using the Open Chest Approach a. General The method of the present invention is suitable for performing a variety of surgical cardiac procedures. The procedures may be performed utilizing an open-chest approach, or through less invasive approaches by the creation of an access space in the chest, or through minimally invasive access utilizing intracoronary and intraventricular catheterization. Dependent on the invasiveness of the approach utilized, the heart can be allowed to pace normally, slowed varying amounts, or stopped completely. A significant period of complete heart stoppage can necessitate the use of supportive cardiopulmonary bypass.

The method of the present invention for performing a coronary artery bypass procedure will now be described in detail. The patient who is to undergo the procedure can be prepared in a conventional manner for cardiac bypass surgery. The patient preparation, anesthesia utilized, and access route to the coronary circulation, will vary depending upon the invasiveness of the specific procedure chosen.

b. Preparation for the Procedure i. General Preparations

Standard techniques of general preparation for open-chest surgery in which cardiopulmonary bypass is utilized have been widely reported. See, e.g. LUDWIG K. VON SEGESSER, ARTERIAL GRAFTING FOR MYOCARDIAL REVASCULARIZATION (1990). In one embodiment of the methods of the invention where an open-chest procedure and cardiopulmonary bypass is utilized, the patient can be prepared for surgery as outlined by Von Segesser.

General preparations for open-chest surgery in which cardiopulmonary bypass is not utilized have been published by Buffolo et al.,61 ANN. THORAC. SURG. 63–66 (1996). In one embodiment of the methods of the invention where an open-chest procedure without cardiopulmonary bypass is utilized, the patient can be prepared for surgery as outlined by Buffolo.

General preparations for closed-chest surgery, to be performed using thoracoscopy and where cardiopulmonary bypass is utilized, have been outlined by Sterman et al., U.S. Pat. No. 5,452,733 (1995). In one embodiment of the methods of the invention where a closed-chest procedure and cardiopulmonary bypass is utilized, the patient can be prepared for surgery as outlined by Sterman.

General preparations for closed-chest surgery to be performed using thoracoscopy, but where cardiopulmonary bypass is not utilized, have been published by Acuff et al., 61 ANN. THORAC. SURG. 135–37 (1996). In one embodiment of the methods of the invention where a closed-chest procedure without cardiopulmonary bypass is utilized, the patient can be prepared for surgery as outlined by Acuff.

As presently known to applicant, general preparations for minimally-invasive coronary artery bypass grafting utilizing intracoronary and intraventricular catheterization and without cardiopulmonary bypass have not been published. Preparations can include the sterile scrubbing and draping of at least one groin to permit access to a femoral artery for catheterization of the coronary vasculature and the sterile scrubbing and draping of the right superior anterior chest wall to permit access to the innominate artery for catheterization of the left ventricle. Further suggested preparations can include those outlined by Sterman and Acuff for thoracoscopic surgery with and without cardiopulmonary bypass, respectively.

ii. Anesthesia Prior to and During the Procedure

Most often, the patient will be placed under general anesthesia prior to the procedure. In one embodiment, standard cardiac operative anesthetic techniques, such as premedication with diazepam, induction with propofol and sufentanil, and maintenance with desflurane can be employed. On occasion, less than general anesthesia can be utilized. Less than general anesthesia is well known in the literature. When the invasiveness of the procedure is minimal, such as when the procedure is to be carried out via intracoronary and intraventricular catheterization, or when the risks of general anesthesia to the individual patient outweighs the risks of less than general anesthesia with regard to the particular procedure planned, less than general anesthesia can be induced. Selective ventilation of the lungs can be achieved through the placement of a double-lumen endobronchial tube which independently provides for the intubation of the left and right mainstem bronchi. An intraesophageal probe can be placed to facilitate cardiac monitoring and the synchronization of power to the laser, when deemed useful.

iii. Access to the Heart and Coronary Vasculature for the Procedure

Following preparation, access to the patient's coronary arterial vasculature can be attained through a variety of techniques, dependent upon the route of access chosen.

Von Segesser has reported a method of access to the coronary arterial vasculature when utilizing an open-chest approach and cardiopulmonary bypass. In one embodiment, utilizing an open-chest approach with cardiopulmonary bypass, access to the coronary vasculature can be obtained as reported by Von Segesser.

Buffolo et al. has reported an open-chest approach to the coronary arterial vasculature when performed without cardiopulmonary bypass. See Buffolo et al.,61 ANN. THORAC. SURG. 63–66 (1996). In one embodiment utilizing an open-chest approach without cardiopulmonary bypass, access to the coronary vasculature can be obtained as reported by Buffolo.

Sterman et al. has reported a method of access to the coronary arterial vasculature when a closed-chest approach with cardiopulmonary bypass is utilized. See Sterman et al., U.S. Pat. No. 5,452,733 (1995). Sterman positions a plurality of access trocar sheaths along the patient's left and right anterolateral chest wall. These trocar sheaths provide access to the coronary vasculature, and allow the temporary repositioning of the heart to facilitate the performance of the procedure. The repositioning is accomplished utilizing grasping tools introduced through the appropriate trocar sheaths. Visualization during this procedure can be either indirectly via thoracoscopy, or directly via a 'window' placed in the left middle anterior chest wall by the surgical removal of the fourth rib. Access to the bypass site can therefore be obtained by following the techniques outlined by Sterman. The instruments to be used in the procedure can also be similar to those described by Sterman.

Acuff et al. has described a method of access to the coronary arterial vasculature when a closed-chest approach without cardiopulmonary bypass is utilized. See Acuff et al., 61 ANN. THORAC. SURG. 135–37 (1996). Similar to the techniques of Sterman, Acuff positions a plurality of access trocar sheaths along the patient's left and right anterolateral chest wall. Also similar to Sterman, Acuff surgically establishes an access space, or window in the left anterior chest wall through the removal of the left fourth rib cartilage. The trocar sheaths, in concert with this window, allow the temporary repositioning of the heart, and access to the coronary arterial vasculature. Visualization during this procedure can be either indirectly via thoracoscopy, or directly via the window. Access to the bypass site can therefore be obtained by following the techniques outlined by Acuff. The instruments to be used in the procedure can also be similar to those described by Acuff.

Access to a chamber of a heart and a coronary artery when the bypass is performed through the minimally invasive approach of intracoronary and intraventricular catheterization can be obtained as follows. Access to a coronary artery can be obtained by the introduction of a catheter into the left or right femoral artery through an arterial cut down procedure. The catheter can then be fed retrograde past the descending aorta, through the ascending aorta, and into the coronary artery by standard catheterization techniques. In a preferred embodiment, access to a chamber of the left side of a heart can be obtained by the introduction of a catheter into the innominate artery, also through an arterial cut down procedure. In the most preferred embodiment, access to the left ventricle is obtained by the introduction of a catheter into the innominate artery and the advancement of this catheter into the left ventricle. In this embodiment, the catheter is advanced through the ascending aorta, past the aortic valve. and into the left ventricle. Techniques by which the left ventricle is catheterized are well known in the literature.

iv. The Procedure

In the coronary artery bypass graft procedures of the present invention, a chamber of a heart provides blood to a coronary artery. The method of the present invention can accomplish this by establishing one or more channels through the wall of a chamber of a heart which lead directly from a chamber of a heart into a coronary artery at a site distal to the narrowing or blockage. The methods of the invention in various embodiments can achieve the establishment of such a channel or channels through a variety of techniques.

Referring now to FIGS. 4, 5, 6, 7, 8, and 9, an exemplary open-chest procedure, to include cardiopulmonary bypass, by which a coronary artery bypass procedure may be accomplished will be described. The open-chest approach affords maximal access to, and visualization of, the coronary vasculature; although at the expense of injury to normal tissue.

Through the methods of the present invention, the device 10, 10' of the present invention, which provides blood from a chamber of a heart 43 directly into a coronary artery 30, is placed. To illustrate the invention, only placement of stent 10 is discussed. It will be appreciated that stent 10' can be similarly placed. In addition, examples will be limited to the embodiment of the apparatus of the invention as illustrated in FIG. 2A.

Preparation for the procedure, and anesthesia prior to and during the procedure, is outlined above.

First, the chest cavity is entered, and pericardium 52 incised anteriorly, to expose a coronary artery 30 (having an obstruction 34) to be bypassed. This is illustrated in FIG. 4.

Second, cardiopulmonary bypass is initiated by a variety of standard techniques as outlined by George Silvay et al., Cardiopulmonary Bypass for Adult patients: A Survey of Equipment and Techniques, 9(4) J. CARDIOTMORAC. VASC. ANESTH. 420–24 (August 1995).

Third, the heart is slowed and/or stopped by a variety of standard techniques. One standard technique is to electrically induce ventricular fibrillation. Another standard technique is warm or cold blood cardioplegia, delivered antegrade or retrograde, and intermittent or continuous, as outlined by Gerald D. Buckberg, Update on Current Techniques of Myocardial Protection, 60 ANN. THORAC. SURG. 805–14 (1995).

Fourth, the heart is inspected and coronary arteries identified. The narrowed or occluded coronary artery 30 can be visually identified, and an appropriate site distal or downstream from the occlusion 34 chosen.

Fifth, blood flow through the target coronary artery 30 is halted by standard techniques. For example, standard techniques include clamping with a arterial clamp. Alternatively, the flow of blood within the coronary artery 30 can be halted by forming a loop around the artery 30 with suture either proximally, or both proximally and distally, and applying appropriate tension on the suture or sutures, or tying the suture or sutures.

Sixth, depending on the degree of exposure deemed necessary, the epicardium overlying the coronary artery at the selected bypass site is incised. This exposure can facilitate locating the lumen of the coronary artery 30 via palpation.

Figure 5:
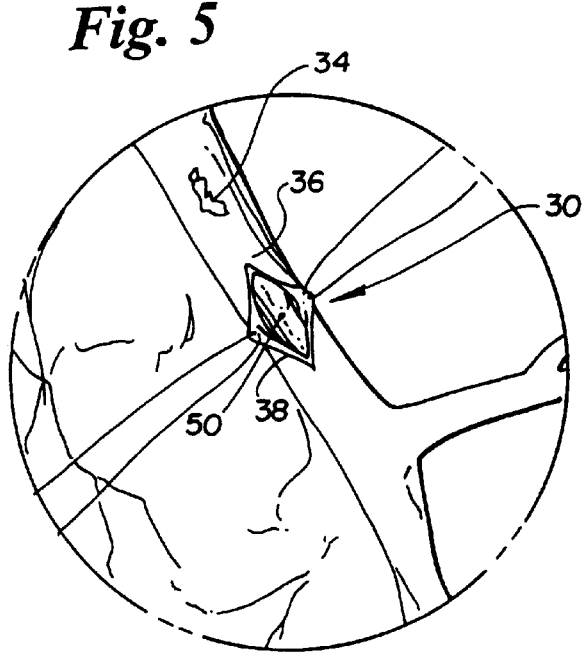
FIG. 5 is a magnified view of area circled 200 in FIG. 4 illustrating a longitudinally incised coronary artery.
Figure 6:
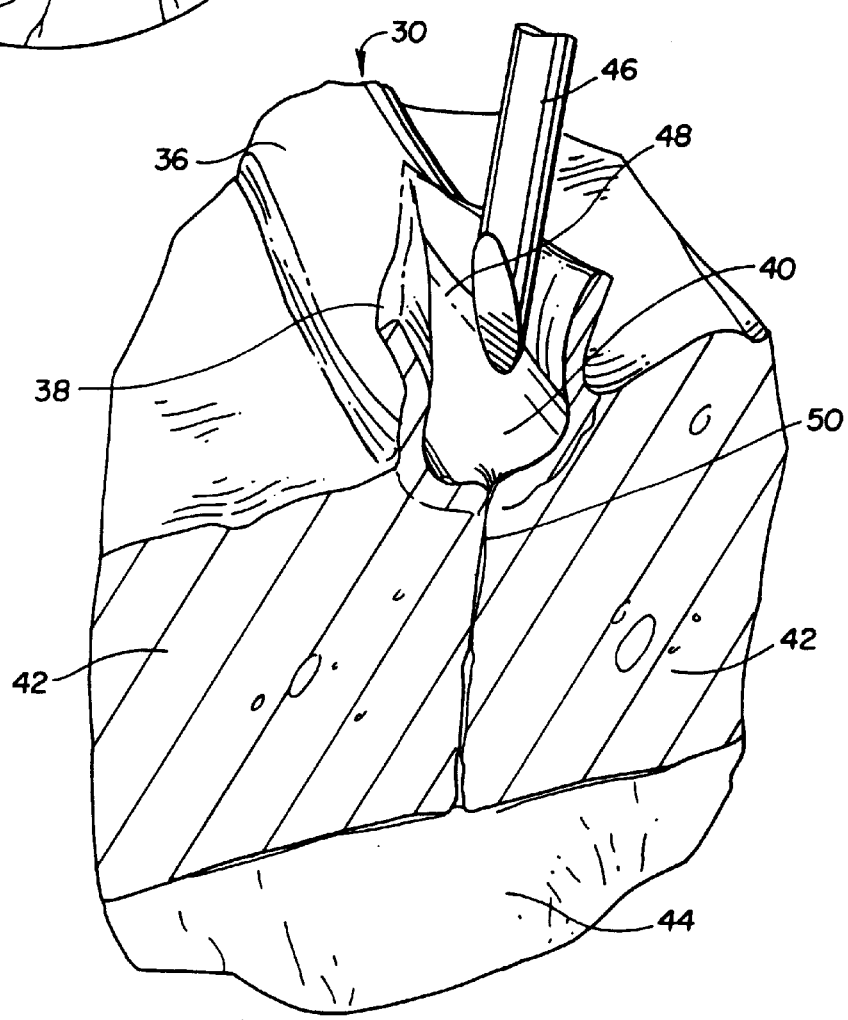
FIG. 6 is a partial external perspective view of a transversely sectioned coronary artery and heart wall illustrating a channel leading from the lumen of a coronary artery and into a chamber of the heart according to the methods of the present invention.

Seventh, as shown in FIG. 5, the superficial wall 36 of the coronary artery 30 is longitudinally incised by standard techniques, such as incision with a scalpel, electrosurgical cutting device, or similar tool; taking care not to damage the deep wall of the artery. This initial incision can be lengthened, if necessary, to accommodate the intracoronary arms 14, 14', 16 of the device 10, 10', using standard tools such as fine angled scissors.

Eighth, a channel, 50, is initiated into the deep coronary arterial wall, 40, and into the musculature, 42, of a chamber of a heart. In the preferred embodiment, a chamber of a heart is a chamber of the left side of the heart. In the most preferred embodiment, a chamber of a heart is the left ventricle. The channel 50 can be initiated by standard techniques such as awl punching, incising, use of a laser, or the like. The channel is then extended into the chamber of a heart, in this case the left ventricle, 44, by standard techniques (such as punching with a trocar 46, incising with a scalpel blade, electrosurgical cutting with an electrosurgical cutting tool, laser or radiofrequency ablation, blunt dissection, etc.).

Ninth, once a channel extending through the entire thickness of a wall 42 of a chamber of a heart is formed, it can be systematically sized by the passage of standard probes.

Tenth, through palpation, inspection, and probing of the distal and proximal coronary artery lumen 48, a device 10, 10', of the present invention of appropriate dimensions is selected, as outlined above.

Figure 7:
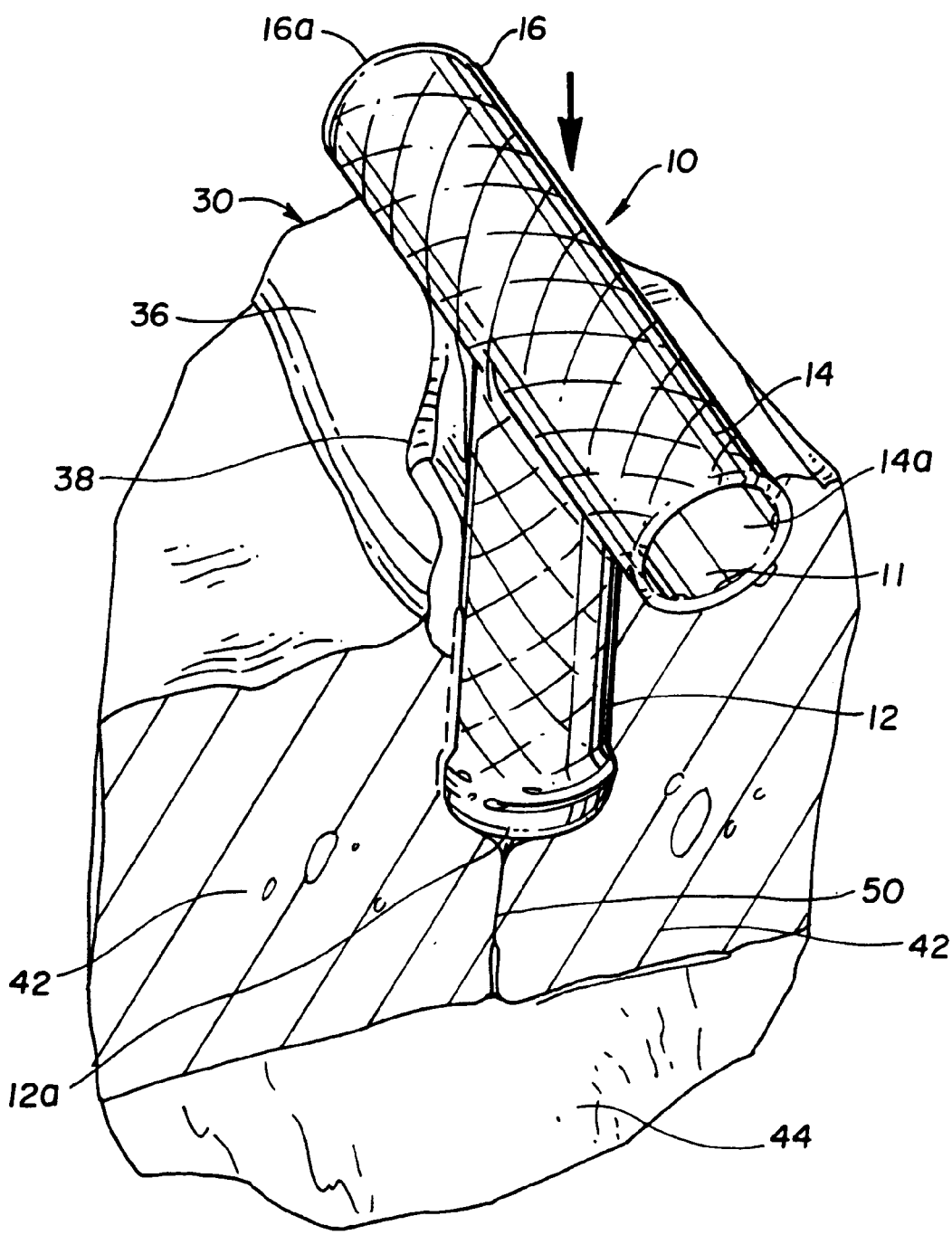
FIG. 7 is a partial external perspective view of a transversely sectioned coronary artery and heart wall illustrating the partial placement of one embodiment of the device of the present invention into the incised coronary artery and formed channel illustrated in FIG. 6.
Figure 8:
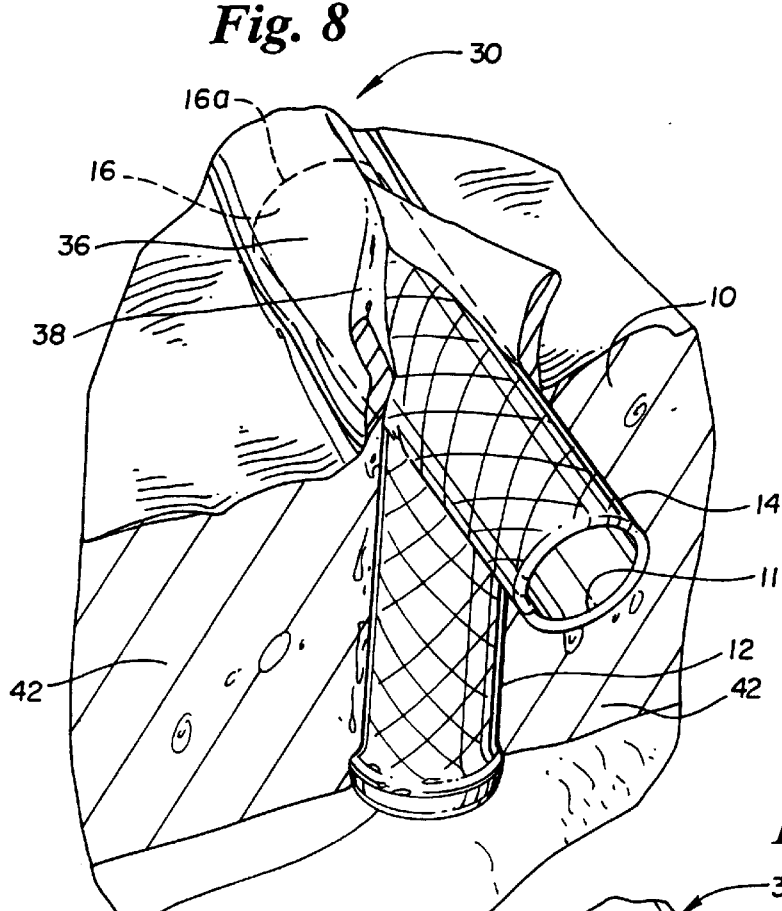
FIG. 8 is a partial external perspective view of a transversely sectioned coronary artery and heart wall illustrating the completed placement of one embodiment of the device of the present invention into the incised coronary artery and formed channel illustrated in FIG. 6.

Eleventh, as illustrated in FIGS. 7 and 8, the anchor arm 12, 12' of the apparatus of the present invention 10, 10' is inserted into the formed channel 50. The one or two remaining arms 14, 14', 16 of the device 10, 10' are then seated within the lumen 48 of the coronary artery 30.

Figure 9:
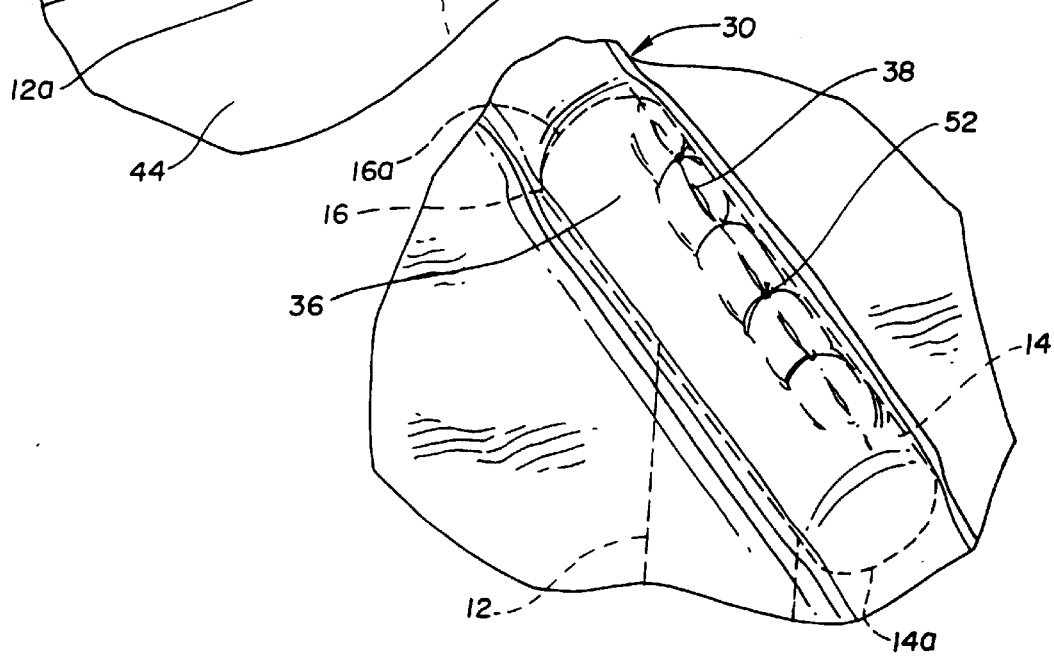
FIG. 9 is a partial external perspective view of a sutured coronary artery and phantom view of the device of the present invention.
Figure 10:
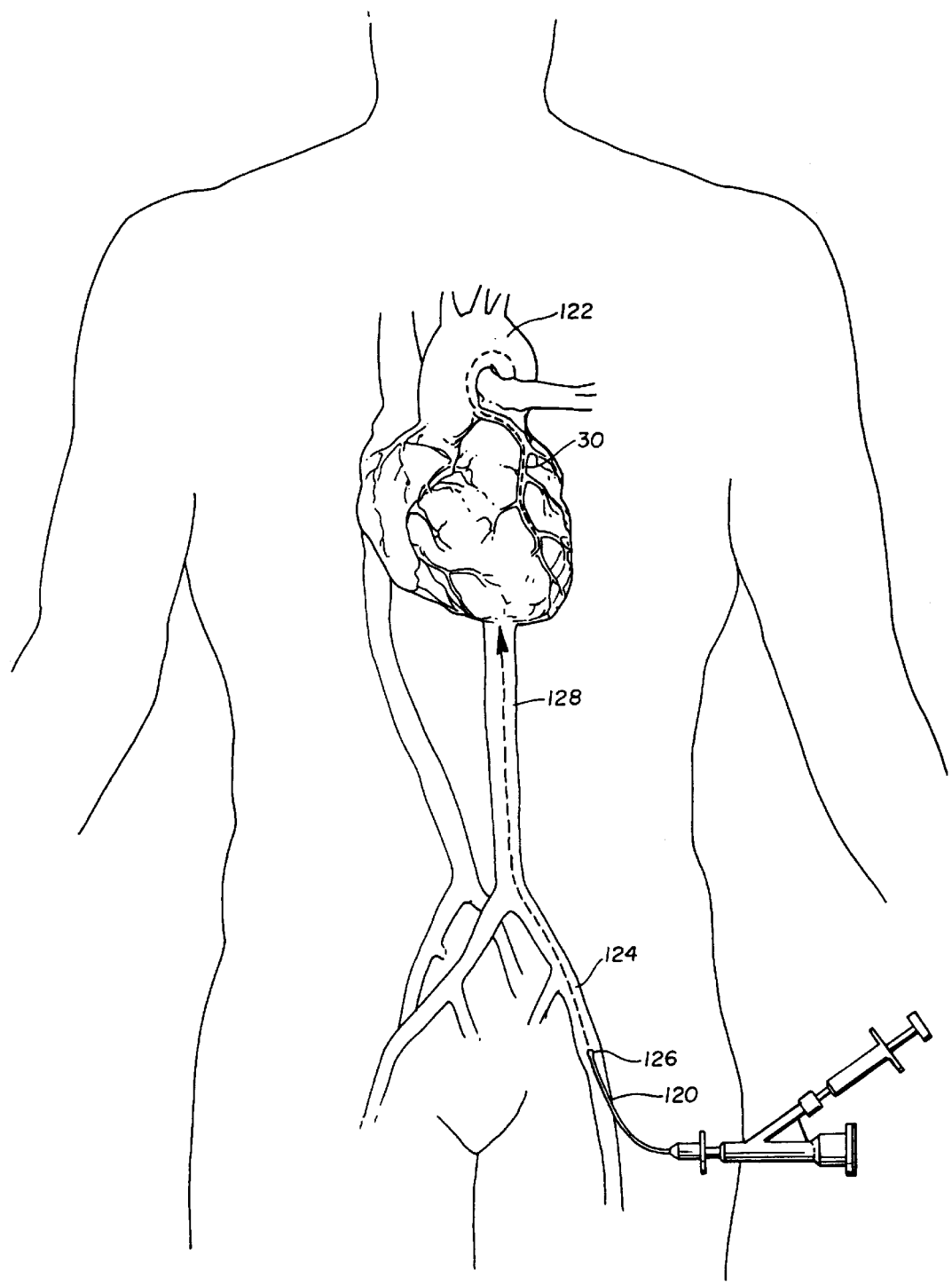
FIG. 10 is a schematic illustration of the use of an endovascular catheter to catheterize the patient's coronary artery.

Twelfth, as shown in FIG. 9, the longitudinal incision 38 previously incised in the anterior wall 36 of the coronary artery 30 is surgically re-aproximated. The re-approximation can be performed by a number of conventional techniques, including suturing 52, laser welding, microstapling, and the like.

Thirteenth, the clamps or sutures closing off blood flow to the coronary artery are released.

Fourteenth, contractions of the heart, are reinitiated by standard electrostimulation or the reversal of cardioplegia.

Fourteenth, the patient is slowly weaned from cardiopulmonary bypass by standard techniques.

Fifteenth, the pericardium, sternum, and overlying skin of the chest is re-approximated and surgically closed by standard, conventional techniques.

Sixteenth, anesthesia is reversed and the patient revived by standard techniques.

D. Embodiments with the Closed Chest Approach

1. The Apparatus of the Present Invention for Use in the Closed Open Chest Approach A closed chest approach according to the method of the present invention may use the stent 10, 10' as described above. Such a procedure will now be described. Following this description, a closed chest approach using alternative embodiments of the apparatus of the invention will be described.

2. The Method of the Present Invention Using the Closed Chest Approach

An exemplary closed-chest procedure, without cardiopulmonary bypass, by which a coronary artery bypass may be accomplished will now be described. The closed-chest approach is less invasive than the open-chest approach, although providing the surgeon with somewhat poorer visualization and limited direct access to both the chambers of the heart and coronary artery bypass site.

Preparation for the procedure, and anesthesia prior to and during the procedure, is outlined above.

First, a plurality of access trocar sheaths is positioned anterior and laterally along the left and right chest walls as outlined by Acuff et al.

Second, a space in the left low anterior chest wall is formed by removal of the fourth rib cartilleage, as outlined by Acuff et al. In this embodiment, the heart and coronary artery can be both directly viewed via this space or window, as well as indirectly visualized via a thoracoscope.

Third, a standard pericardiotomy is performed using a scalpel or electrosurgical cutting tool introduced through the left lateral chest trocar sheaths while viewing under thoroacoscopy. The pericardium can be excised and either spread open, or removed from the thoracic cavity as outlined by Acuff et al.

Fourth, if necessary, the can be rotated within the mediastinum. Direct access and visualization through the formed chest wall space can require rotation of the heart. Rotation of the heart can be accomplished by the grasping of the heart by tools inserted through access trocar sheaths located along the left and right chest wall as described by Sterman et al. Alternatively, traction on sutures placed in the pericardium can distract the heart allowing appropriate direct visualization of the area to be bypassed as described by Acuff et al.

Fifth, once the coronary artery to be bypassed is identified and well-visualized; snare sutures of 5–0 polypropylene are placed proximally and distally to the target area as described by Acuff et al.

Sixth, the heart rate can be slowed to approximately 40 beats/minute by the intravenous administration of esmolol or diltiazem to minimize motion within the operative field as described by Acuff etal. Nitroglycerin and heparin can also be administered to reduce cardiac ischemia and prevent clotting respectively as outlined by Acuff et al.

Because cardiopulmonary bypass is omitted in this embodiment, intermittent coronary artery occlusion to induce ischemic preconditioning, as well as transesophageal echocardiography to review cardiac wall motion changes, can be utilized as described by Acuff et al. The epicardium can be incised over the area selected for bypass and the anterior surface of the artery cleared under direct visualization through the space or window, or via remote instruments inserted through the trocar sheaths under thoracoscopic guidance.

Seventh, in situations where the coronary artery can be directly viewed, the lumen 48 of the coronary artery is identified by palpation. Either under direct visualization, or under thoracoscopic guidance and using instruments manipulated through the trocar sheaths, the superficial wall 36 of the coronary artery is then longitudinally opened. As above, care is taken to leave the deep wall 40 of the artery undamaged. The incision 38 can be enlarged, as necessary, to accommodate the intracoronary arms 14, 14', 16 of the device 10, 10' of the present invention using fine angled scissors. This enlargement can be performed with standard surgical scissors under direct viewing through the window, or via other surgical instruments remotely manipulated following their insertion through the trocar sheaths.

Eighth, a channel 50 through the heart wall is initiated by incising or laser ablating into the deep wall 40 of the coronary artery. This also can be performed by standard surgical tools under direct viewing, or by the remote manipulation of specialized instruments introduced through the trocar sheaths and viewed thoracoscopically. The channel 50 is then extended through the deep coronary arterial wall 40, through underlying cardiac musculature 42, and into the underlying chamber of the heart 44 by incising with a scalpel or electrosurgical cutting blade, laser ablation, blunt dissection, or the like. In the preferred embodiment, a chamber of a heart 44 is one of the two chambers of the left side of the heart. In the most preferred embodiment, a chamber of a heart 44 is the left ventricle.

Ninth, the channel 50 extending through the entire thickness of a muscular wall 42 can be systematically sized by the passage of standard measuring probes. These standard measuring probes, with fixed and known tip diameters, can be similarly used to size and determine the proximal and distal patency of the coronary artery being bypassed.

Tenth, through direct and/or thoracoscopic inspection of the coronary artery lumen 48, or by probing as outlined above, an appropriately dimensioned device 10, 10' of the present invention is selected. As in the case of the open-chest approach (outlined above), an array of devices 10, 10' of various sizes can be available for the operation.

Eleventh, either under direct control and visualization, or by indirect manipulation and thoracoscopic viewing, the anchoring arm 12, 12' of the apparatus 10, 10' of the invention is inserted into the formed channel 50. By similar techniques the remaining intracoronary arm or arms 14, 14', 16 of the apparatus 10, 10' n are seated within the lumen 48 of the coronary artery 30 being bypassed. In one embodiment where the procedure is performed under thoracoscopic viewing, the device 10, 10' can be introduced into the cardiac cavity through the space or window previously formed within the anterior inferior aspect of the left chest wall. In this embodiment, the device 10, 10' can be grasped, once introduced into the chest cavity, by surgical instruments inserted through the trocar sheaths and remotely manipulated into position. In this manner the anchor arm 12, 12' of the device 10, 10' is then inserted into the channel formed 50 via the remote manipulation of these instruments.

Twelfth, the incision present in the superficial wall 38 of the coronary artery 30 is closed by conventional surgical techniques such as suturing, laser welding, microstapling, and the like. When closure is by indirect thoracoscopic versus direct viewing, suturing, laser welding, microstapling and the like can be accomplished by utilizing surgical instruments remotely manipulated following their introduction through the trocar sheaths.

Thirteenth, upon completion of placement of the device 10, 10' of the present invention, the heart, if rotated, can be returned to its normal orientation.

Fourteenth, all heart manipulating devices are removed from the chest cavity.

Fifteenth, contractions of the heart can be allowed to return to their normal resting rate by the discontinuation of intravenous esmolol and diltiazem, if utilized.

Sixteenth, the pericardium 52 is partially or completely re-approximated. An external drain can be placed inside the pericardium, as needed, as described by Acuff et al.

Seventeenth, the trocar sheaths are removed, and all thoracic punctures surgically repaired in a conventional manner.

Eighteenth, anesthesia is reversed and the patient revived by standard techniques.

E. Embodiments with the Catheter-Controlled Approach

Referring now to FIGS. 10, 11, 12, 13, 14, 15, and 16, an exemplary coronary artery bypass procedure performed through catheterization will be described. This approach allows no direct visualization of the coronary vasculature, although the chamber of the heart could be indirectly visualized during the procedure by equipping the intraventricular catheter with a standard fiber-optic device, if desired. Because the procedure is performed through catheters introduced remotely, normal tissue injury is minimized.

Preparation for the procedure, and anesthesia prior to and during the procedure, is outlined above.

In the embodiment to be described, cardiopulmonary bypass is unnecessary. However, the procedure would be in no way limited if cardiopulmonary bypass were performed.

First, an intracoronary catheter 120 (FIG. 10) is inserted via an incision in the groin 126 and advanced within the femoral artery 124. Through continued advancement within the descending aorta 128, and the ascending aorta 122, the coronary artery 30 is entered.

Dependent on the degree of narrowing or occlusion of the coronary artery, standard angioplasty, atherectomy, or some similar procedure can be optionally performed if passage of the catheter tip 136 (FIG. 11A) is hindered. Angioplasty, arthrectomy, and the like could optionally precede the catheter-controlled bypass procedure.

If desired, the heart may be slowed while catheterizing the coronary vasculature, during the construction of a channel or channels 50 leading from a chamber of a heart 44 into a lumen of a coronary artery 30 itself, or both. Such slowing can improve visualization of the catheters as facilitated by fluoroscopy or the alternative radiologic techniques by which the procedure can be performed. Standard pharmacologic methods, as described above, to slow the heart are well known in the literature.

Second, the intracoronary catheter 120 is advanced within the coronary arterial vasculature tree to the target location through standard catheter manipulation techniques. The proper location of the intracoronary catheter tip 136 in relation to the targeted bypass site can be determined through standard radiographic techniques.

Figure 11A:
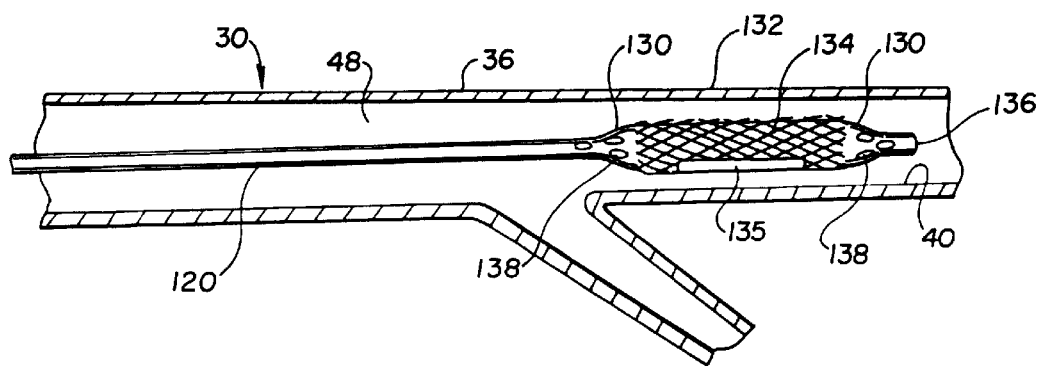
FIG. 11A is a cutaway side elevation view of the coronary artery of the bypass procedure illustrating the intravascular catheter with distally-located stent prior to inflation of the catheter balloon underlying the stent.
Figure 11B:
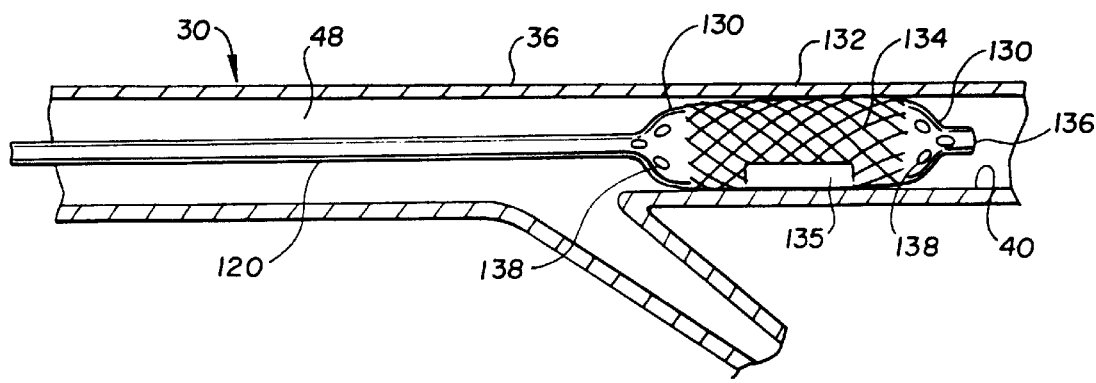
FIG. 11B is a cutaway side elevation view of the coronary artery of the bypass procedure illustrating the intravascular catheter with distally-located stent following inflation of the catheter balloon underlying the stent.
Figure 11C:
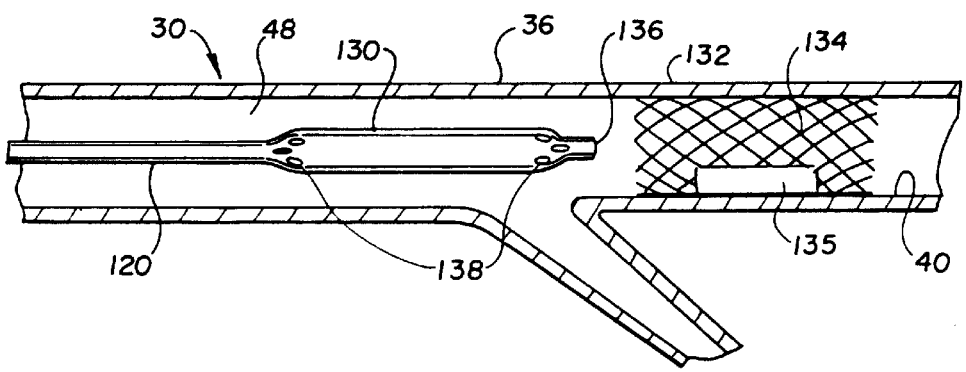
FIG. 11C is a cutaway side elevation view of a coronary artery illustrating the stent seated to the walls of the coronary artery and the catheter partially withdrawn following deflation of the catheter balloon.

Third, as shown in FIGS. 11A–11C, a balloon 130 located on the distal end of the intracoronary catheter 120 is inflated (FIG. 11B). Inflation of the balloon 130 causes a stent 134 located circumferentially surrounding the balloon 130 to be seated against the coronary arterial walls 36, 40. The stent 134 is a hollow expandable stent having a cut-out area 135 along the cylindrical wall of the stent 134, for reasons that will become apparent. The stent 134 is positioned at placement within the coronary artery in a manner that the cut-out 135 is juxtaposed against the deep wall 40 of the coronary artery 30 upon inflation of the intracoronary catheter balloon 130.

Fourth, the balloon 130 is deflated (FIG. 11C) and the catheter 120 withdrawn into the ascending aorta 122 leaving the expanded stent 134 in place.

Figure 12:
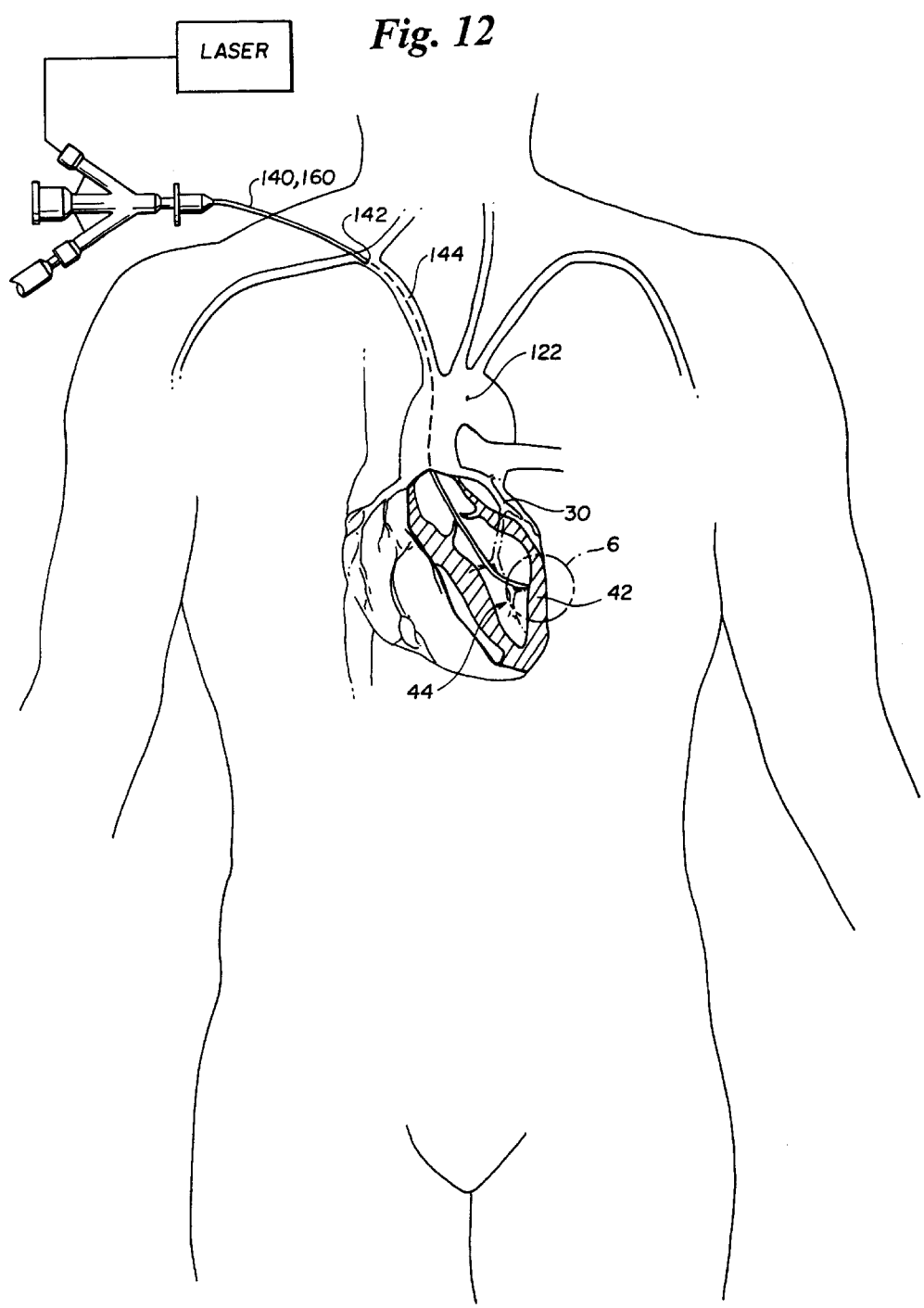
FIG. 12 is a schematic illustration with the heart in partial cutaway of the use of an endovascular catheter to catheterize the patient's left ventricle.
Figure 13A:
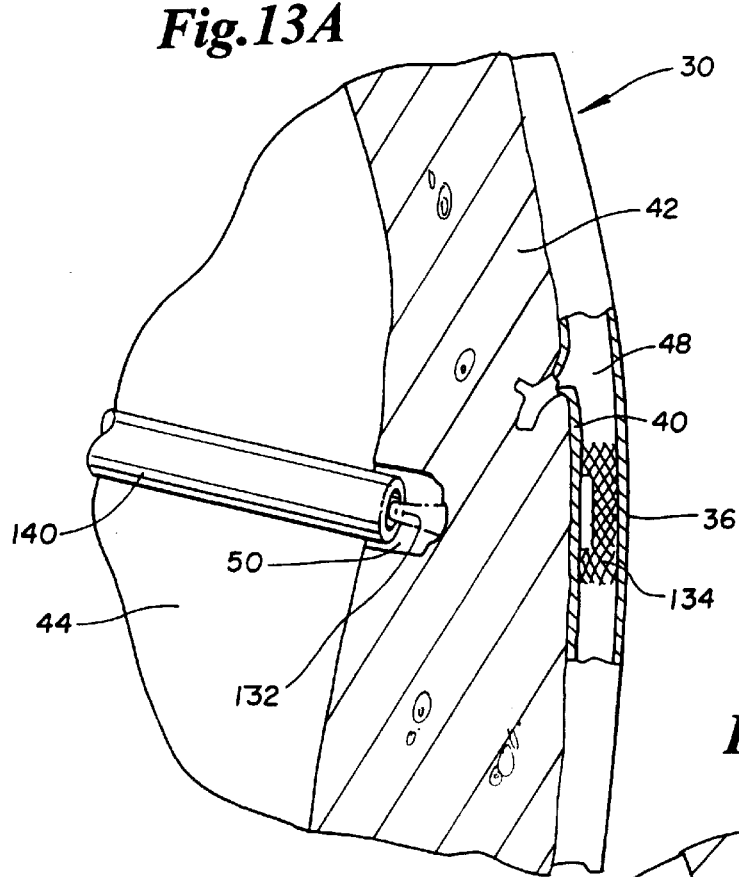
FIG. 13A is a cutaway view of the left ventricle and a partial cutaway view of the coronary artery with seated stent illustrating the formation of the channel into the wall of the left ventricle.
Figure 13B:
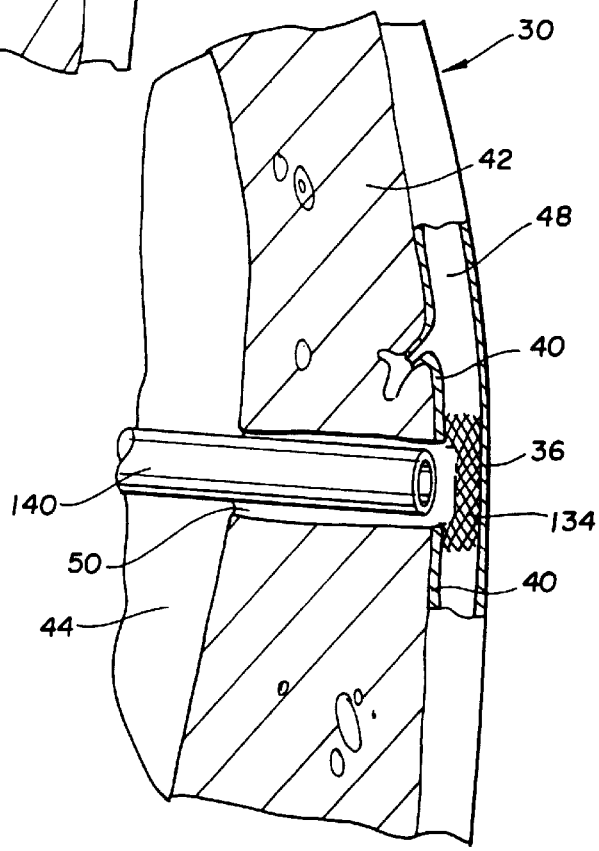
FIG. 13B is a cutaway view of the left ventricle and a partial cutaway view of the coronary artery with seated stent illustrating the completed channel through the wall of the left ventricle and deep wall of the coronary artery at the chosen bypass site.

Fifth, an intraventricular catheter 140 is inserted into the innominate artery 144 via an incision in the anterior superior right chest wall 142 as shown in FIG. 12. The intraventricular catheter 140 is advanced in a retrograde fashion through the ascending aorta 22, and into the chambers of the left side of the heart. By continued advancement, the intraventricular catheter 140 is extended past the semilunar valves 148 and into the left ventricle 44. Throughout the procedure, the location of the intraventricular catheter 140 within a chamber of a heart 44 can be ascertained by either indirect visualization employing standard fiber-optic instrumentation inherent to the intraventricular catheter, or and/or by standard radiographic techniques.

Sixth, a channel 50 can be ablated (FIGS. 13A–13B) through both a wall of a chamber of a heart 42 and the deep wall of a coronary artery 40 utilizing an ablating tip 132. Such ablating devices are well known in the literature and can include a laser, a radiofrequency device, or the like. Power to the ablating tip 132 can be synchronized via the intraesophageal probe such that ablation occurs at a recurring aspect of the cardiac cycle. Such synchronization of devices to physiological function is well-known in the literature. The ablation can be indirectly observed via fiber optics associated with the intraventricular catheter 140. Alternatively, the location of the ablating tip 132 can be determined by standard radiographic techniques.

Seventh, once a channel 50 through the heart chamber wall 42 is formed, the intracoronary catheter 120 is re-advanced into the coronary artery 30.

Figure 14A:
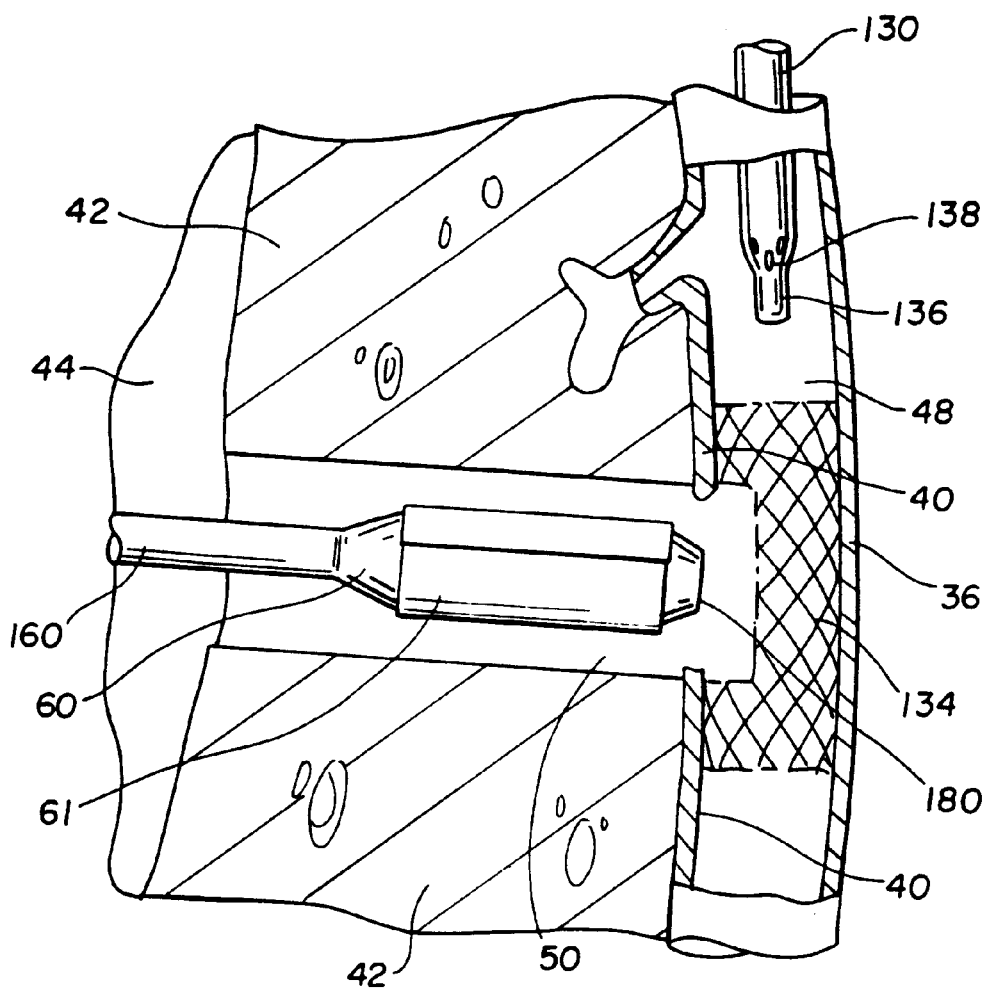
FIG. 14A is a cross-sectioned view of the left ventricle and a partial cutaway view of the coronary artery with seated stent illustrating the placement of the second intraventricular catheter within the formed channel.
Figure 14B:
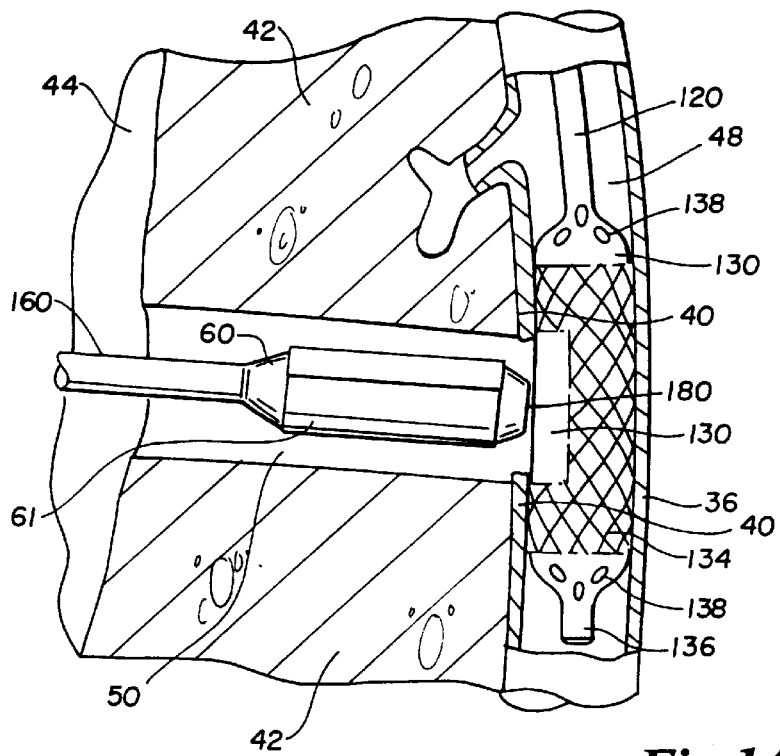
FIG. 14B is a cross-sectioned view of the left ventricle and a partial cutaway view of the coronary artery with seated stent illustrating the blockage of the formed channel by the re-inflated balloon of the intracoronary catheter.

Eighth, the balloon 130 on the distal end of the intracoronary catheter 120 is re-inflated upon reaching the target bypass site, as illustrated in FIGS. 14A and 14B. Inflation of the intracoronary catheter balloon 130 seals the formed channel 50 so that blood is prevented from flowing from the coronary artery lumen 48, through the formed channel 50, and into a chamber of the heart 44. Note, though, that the inflation of the intracoronary catheter balloon 130 still allows blood to perfuse the downstream portion of the coronary artery 30. This is because the intracoronary catheter 120 is equipped with channels 138 which allow blood to pass internally within the intracoronary catheter 120 from the upstream portion of the coronary artery 30, and to exit the catheter into the downstream portion of the coronary artery 30.

Ninth, the ablating catheter 140 is removed from the body completely.

Tenth, a second intraventricular catheter 160 is inserted into the innominate artery 144 at the arterial cut-down site 142, as shown in FIG. 12. The intraventricular catheter 160 is next advanced in a retrograde fashion into the ascending aorta 22. By continued advancement, the intraventricular catheter 160 is finally extended past the semilunar valves 148 and into the left ventricle 44.

This intraventricular catheter is equipped with a inflatable balloon 60 on the catheter's distal end, and a stent-forming device 61 circumferentially surrounding the balloon 60 on the catheter's distal end (FIGS. 14A–14D).

Figure 15A:
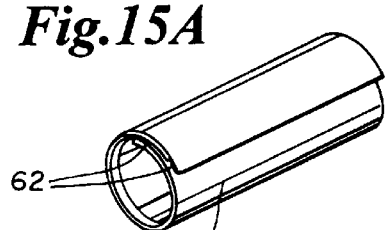
FIG. 15A is a right anterior superior perspective view of the device placed within the formed channel in its spiral shape.
Figure 15B:
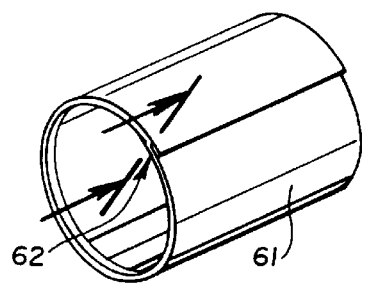
FIG. 15B is a right anterior superior perspective view of the device placed within the formed channel in its cylindrical form.

The stent forming device 61 is a spiral sheet shown seperately in FIGS. 15A and 15B. Initially, the device 61 is a sheet formed in a spiral shape as shown in FIG. 15A to present a reduced diameter smaller than the diameter of the formed channel 50. In response to expanding forces (e.g., expansion of a balloon 60 within device 61), device 61 expands to a cylinder as shown in FIG. 15B. Interlocking tabs 61a and recesses 61b on opposing edges of the device 61 define a locking mechanism 62 to retain the device 61 in a cylindrical shape. The cylindrical shape of device 61 after expansion of the balloon 60, as shown in FIG. 15B, is larger in diameter than the spiral shape of device 61 prior to expansion of the balloon 60, as shown in FIG. 15A. The device 61 as expanded is sized to be retained within the formed channel 50 upon expansion.

Throughout this portion of the procedure, the location of this second intraventricular catheter 160 within a chamber of a heart 44 can be ascertained by either indirect visualization employing standard fiber-optic instrumentation inherent to the second intraventricular catheter, or and/or by standard radiographic techniques.

Eleventh, the tip 180 (FIG. 14A) of the second intraventricular catheter 160 is introduced into and advanced within the formed channel 50.

Figure 14C:
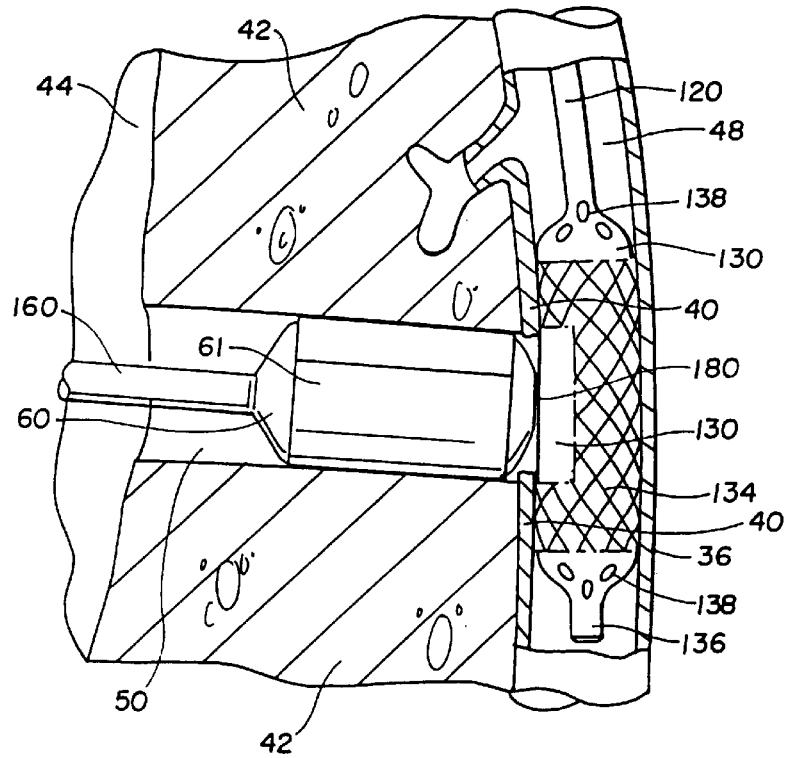
FIG. 14C is a cross-sectioned view of the left ventricle and a partial cutaway view of the coronary artery with seated stent illustrating the inflation of the balloon located on the distal end of the intraventricular catheter and the seating of the overlying spiral-shaped device against the walls of the formed channel.
Figure 14D:
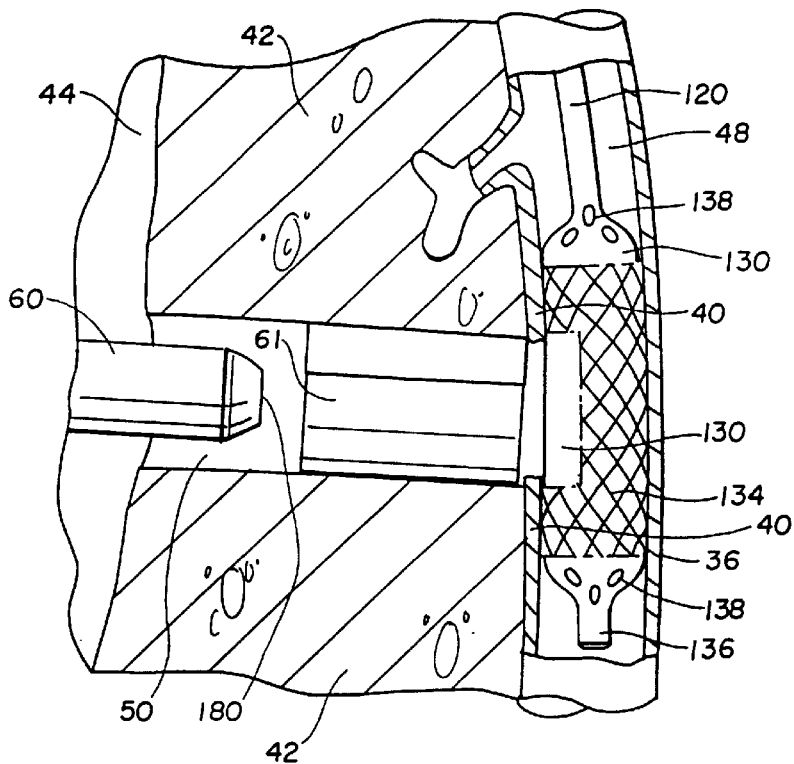
FIG. 14D is a cross-sectioned view of the left ventricle and a partial cutaway view of the coronary artery with seated stent illustrating the device in its locked cylindrical shape seated against the channel walls and the partially withdrawn second intraventricular catheter.

Twelfth, with the tip 180 of the second intraventricular catheter 160 near or abutting the side of the intracoronary catheter balloon 130, a balloon 60 surrounding circumferentially the tip of the second intraventricular catheter 160, is inflated. As shown in FIGS. 14C and 14D, inflation of the balloon 60 causes the device 61 located circumferentially around the balloon 60 located on the end of the second intraventricular catheter 160 to become seated against the walls of the formed channel 50.

Figure 16:
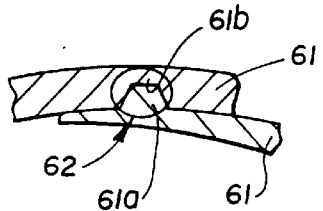
FIG. 16 is a cross-sectional view of the interlocking mechanism of the device of FIGS. 15A and 15B in its locked position.

As shown in FIG. 16, the device 61, is locked into the cylindrical position when the underlying balloon 60 is inflated by an interlocking mechanism 62 constructed as part of the device 61.

Thirteenth, the balloon 60 on the intraventricular catheter tip is deflated, and the catheter removed from the body, as shown in FIG. 14D.

Fourteenth, a third intraventricular catheter 70 is inserted at the innominate artery access site 142. This third intraventricular catheter 70 is then advanced in a retrograde fashion into a chamber of the left side of a heart, as outlined above.

Figure 17A:
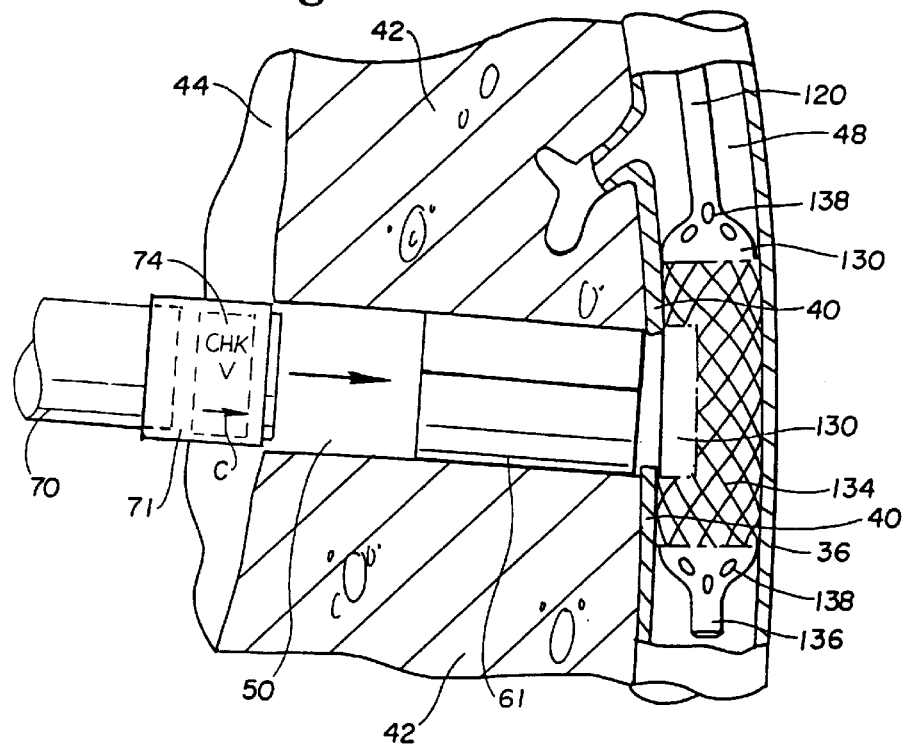
FIG. 17A is a cross-sectioned view of the left ventricle and a partial cutaway view of the coronary artery, with the device shown in FIGS. 15A and 15B seated within the formed channel, illustrating the introduction of the third intraventricular catheter into the formed channel.
Figure 17B:
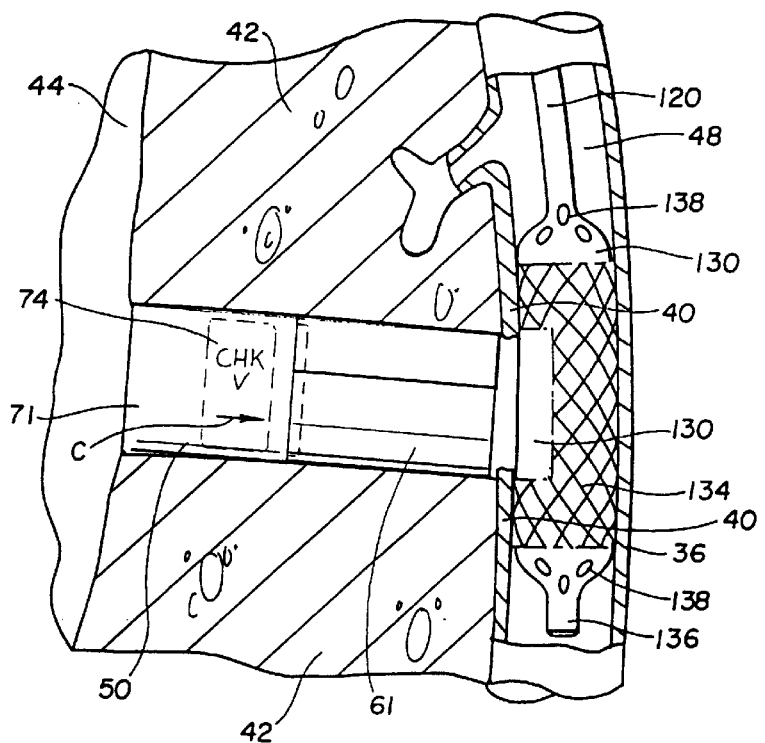
FIG. 17B is a cross-sectioned view of the left ventricle and a partial cutaway view of the coronary artery, with the device shown in FIGS. 15A and 15B seated within the formed channel, illustrating the tongue and groove interlocking of the check-valve equipped device to the device seated within the formed channel.

This.third intraventricular catheter 70 is equipped with a hollow tube 71 on its distal tip which can interlock to the device 61 previously placed within the formed channel 50, as shown in FIGS. 17A and 17B.

Fifteenth, the hollow tube 71 is forwarded within the formed channel 50, and interlocked to the device 61. In one embodiment, the hollow tube 71 can partially insert into the device 61 previously seated within the formed channel 50.

The hollow tube 71 can, but may not necessarily, be equipped with a one-way check valve 74 to limit blood flow to ther direction of arrow C. An array of such hollow tubes 71 of various dimensions can be available to the surgeon at the operative procedure.

Sixteenth, the balloon 130 on the end of the intracoronary catheter 120 is deflated.

Seventeenth, angiographic dye can be introduced into a chamber of the heart through a port internal to the third intraventricular catheter 71. The introduction of angiographic dye can allow the blood flow to be visualized under fluoroscopy, digital subtraction angiography, or similar standard techniques. By such radiographic examination, blood flow directly from a chamber of a heart into a coronary artery can be ascertained. In cases where a check valve 74 is utilized, the uni-directional flow from a chamber of a heart and into a coronary artery, in the direction of arrow C, can be verified.

Eighteenth, the third intraventricular catheter 70 is withdrawn from the body through the innominate incision site 142.

Nineteenth, the intracoronary catheter 120 is withdrawn from the body through the femoral incision site 126.

Twentieth, the sites of the innominate incision 142 and femoral incision 126 are surgically re-approximated through standard closure techniques.

Twenty-first, anesthesia is reversed and the patient revived by standard techniques.

CHANGES AND MODIFICATIONS

Although the foregoing invention has been described in detail by way of illustration and example, for purposes of clarity of understanding, it will be obvious that changes and modifications may be practiced within the scope of the appended claims.

What is claimed is:

1. An apparatus for use in a coronary artery bypass procedure at a coronary vessel disposed lying at an exterior of a heart wall, the apparatus comprising;

a hollows blood flow conduit having a first end sized for being inserted into and retained within the cart wall of a heart chamber containing oxygenated blood with said first end sized to span a thickness of the heart wall with an opening of the first end in blood-flow communication with blood contained within the chamber, said first end having sufficient radial rigidity to resist collapse of said first end in response to contraction of said heart;

the conduit having a second end sized for being inserted within the coronary vessel with an opening of the second end in blood flow communication with a lumen of the coronary vessel, said second end having an open cell structure within said vessel; and the conduit defining a blood flow path between the openings of the first and second ends.

2. An apparatus according to claim 1 wherein the conduit is a substantially L-shaped tube.

3. An apparatus according to claim 1 wherein the conduit is a substantially T-shaped tube.

4. An apparatus according to claim 1, wherein the first end of the conduit protrudes beyond an interior surface of the heart wall.

5. An apparatus according to claim 1 wherein the blood flow path closes at least once during a cycle of the heart.

6. An apparatus according to claim 5 wherein the conduit includes a valve to close during diastole.

7. An apparatus according to claim 1 wherein the second end is radially expandable within the vessel.

8. An apparatus according to claim 7 wherein the first end is radially expandable within the heart wall.

9. An apparatus for use in a coronary artery bypass procedure at a coronary vessel disposed lying at an exterior of a heart wall, the apparatus comprising;

a hollow blood flow conduit having a first end sized for being inserted into and retained within the heart wall of a heart chamber containing oxygenated blood with said first end sized to span a thickness of the heart wall with an opening of the first end in blood flow communication with blood contained within the chamber, said firs end having sufficient radial rigidity to resist collapse of said first end in response to contraction of said heart;

the conduit having a second end sized for being inserted within the coronary vessel with an opening of the second end in blood flow communication with a lumen of the coronary vessel, said second end having an open cell structure within said vessel; and the conduit defining a blood flow path between the openings of the first and second ends, wherein the conduit includes a reservoir for accumulating blood from the conduit during periods of high blood pressure and for discharging accumulated blood into the conduit during periods of low blood pressure.

10. An apparatus according to claim 9, wherein the first end of the conduit protrudes beyond an interior surface of the heart wall.

11. A method for performing a coronary bypass procedure at a coronary vessel disposed lying on an exterior of a heart wall of a having a heart having a heart chamber, the method comprising:

A. selecting a hollow blood flow conduit having:
  a. a first end sized for being inserted into and retained within the heart wall of a heart chamber containing oxyenated blood with an opening of the first end in blood-flow communication with blood contained within the chamber;
  b. the conduit having a second end sized for being inserted into the coronary vessel with an opening of the second end in blood flow communication with a lumen of the coronary vessel, said second end having an open cell structure within said vessel; and
  c. the conduit defining a blood flow path between the openings of the first and second ends, B. inserting the first end of the conduit through the heart wall with the first end in blood flow communication with the heart chamber;

C. placing the second end of the conduit into the vessel with openings of the open cell structure opposing an interior wall of the vessel.

12. A method according to claim 11 wherein the blood flow path is formed by placing the conduit through a deep wall of the coronary vessel.

13. A method according to claim 11 wherein the coronary vessel is a coronary artery.

14. A method according to claim 11 comprising closing the blood flow path once per cycle of the heart.

15. A method according to claim 11 wherein the blood flow path is closed during diastole.

16. A method according to claim 11 Wherein the second end is radially expanded within the vessel.

17. A method according to claim 16 wherein the first end is radially expanded within the heart wall.

18. The method of claim 11, wherein the heart is a human heart.

19. The method of claim 11, wherein the conduit remains in the heart.

20. The method of claim 11 further comprising the steps of: closing an incision made during insertion of the conduit and leaving the conduit in the heart.

21. The method of claim 11 further comprising the steps of: withdrawing a catheter used to deliver the conduit and leaving the conduit in the heart.

22. An apparatus for use in a coronary artery bypass procedure at a coronary vessel disposed lying at an exterior of a heart wall, the apparatus comprising;

a blood flow conduit having a first end sized for being inserted into and retained within the heart wall of a heart chamber containing oxygenated blood with said first end sized to span a thickness of the heart wall with an opening of the first end in blood-flow communication with blood contained within the chamber, said first end having a solid wall construction within said heart wall and sufficient radial rigidity to resist collapse of said first end in response to contraction of said heart;

the conduit having a second end sized for being inserted within the coronary vessel with an openig of the second end in blood flow communication with a lumen of the coronary vessel, said second end having an open cell structure within said vessel; and tile conduit defining a blood flow path between the openings of the first and second ends.

23. An apparatus according to claim 22, wherein the first end of the conduit protrudes beyond an interior surface of the heart wall.

24. A method for performing a coronary bypass procedure at a coronary vessel disposed lying on an exterior of a heart wall of a heart having a heart chamber, the method comprising:

A. selecting a hollow blood flow conduit having:
  a. a first end adapted to be inserted into and retained within the heart wall of a heart chamber containing oxygenated blood with an opening of the first end in blood flow communication with blood contained within the chamber, said first end having a sufficient radial rigidity to resist collapse of said first end in response to contraction of said heart, wherein said first end remains open during both systole and diastole;
  b. the conduit having a second end sized to be inserted into the coronary vessel with an opening of the second end in blood flow communication with a lumen of the coronary vessel, said second end having an open cell structure within said vessel; and
  c. the conduit defining a blood flow path between the openings of the first and second ends;

B. inserting the first end of the conduit through the heart wall with the first end in blood flow communication with the heart chamber;

C. placing the second end of the conduit into the vessel with openings of the open cell structure opposing an interior wall of the vessel.

25. The method of claim 24, wherein the heart is a human heart.

26. The method of claim 24, wherein the conduit remains in the heart.

27. The method of claim 24 further comprising the steps of closing an incision made during insertion of the conduit and leaving the conduit in the heart.

28. The method of claim 24 further comprising the steps of: withdrawing a catheter used to deliver the conduit and leaving the conduit in the heart.

* * * * *

UNITED STATES PATENT AND TRADEMARK OFFICE
CERTIFICATE OF CORRECTION

PATENT NO. : 6,361,519 B1
DATED : March 26, 2002
INVENTOR(S) : Knudson et al.

It is certified that error appears in the above-identified patent and that said Letters Patent is hereby corrected as shown below:

<u>Title page,</u>
Item [56], U.S. PATENT DOCUMENTS, reference "5,353,744 10/1994" should read -- 5,653,744 08/1997 --
OTHER PUBLICATIONS, reference "Toshiyuki Beppu, ME et al.," "Surery" should read -- Surgery --
Reference "George Silvay", "Vasuclar" should read -- Vascular --

<u>Column 15,</u>
Line 8, "n limits" should read -- limits --
Line 29, "31' n less" should read -- 31' less --
Line 55, "11' n of arm" should read -- 11' of arm --

<u>Column 22,</u>
Line 54, "10' n are" should read -- 10' are --

<u>Column 25,</u>
Line 52, "This.third" should read -- This third --

<u>Column 26,</u>
Line 33, "a hollows blood" should read -- a hollow blood --
Line 34, "the cart wall" should read -- the heart wall --

<u>Column 27,</u>
Line 4, "said firs" should read -- said first --
Line 23, "wall of a having a heart having a heart chamber," should read -- wall of a heart having a --

UNITED STATES PATENT AND TRADEMARK OFFICE
CERTIFICATE OF CORRECTION

PATENT NO. : 6,361,519 B1
DATED : March 26, 2002
INVENTOR(S) : Knudson et al.

It is certified that error appears in the above-identified patent and that said Letters Patent is hereby corrected as shown below:

<u>Column 28,</u>
Line 7, "a blood flow" should read -- a hollow blood flow --
Line 21, "tile conduit" should read -- the conduit --

Signed and Sealed this

Eighteenth Day of March, 2003

JAMES E. ROGAN
*Director of the United States Patent and Trademark Office*